US009636656B2

(12) United States Patent
Dougherty et al.

(10) Patent No.: US 9,636,656 B2
(45) Date of Patent: May 2, 2017

(54) CAGED COMPOUND DELIVERY AND RELATED COMPOSITIONS, METHODS AND SYSTEMS

(71) Applicants: CALIFORNIA INSTITUTE OF TECHNOLOGY, Pasadena, CA (US); UNIVERSITY OF SOUTHERN CALIFORNIA, Los Angeles, CA (US)

(72) Inventors: Dennis A. Dougherty, Pasadena, CA (US); Robert H. Grubbs, South Pasadena, CA (US); Mark Humayun, Glendale, CA (US); Clinton J. Regan, Los Angeles, CA (US); Azita Emami, Pasadena, CA (US)

(73) Assignees: CALIFORNIA INSTITUTE OF TECHNOLOGY, Pasadena, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 14/362,888

(22) PCT Filed: Dec. 7, 2012

(86) PCT No.: PCT/US2012/068626
§ 371 (c)(1),
(2) Date: Jun. 4, 2014

(87) PCT Pub. No.: WO2013/086457
PCT Pub. Date: Jun. 13, 2013

(65) Prior Publication Data
US 2014/0308208 A1 Oct. 16, 2014

Related U.S. Application Data

(60) Provisional application No. 61/568,046, filed on Dec. 7, 2011.

(51) Int. Cl.
*A61K 41/00* (2006.01)
*A61K 49/00* (2006.01)
*B01J 19/12* (2006.01)
*A61K 9/00* (2006.01)
*A61K 47/48* (2006.01)
*A61N 5/06* (2006.01)
*C07C 59/66* (2006.01)
*C07D 209/12* (2006.01)
*C07D 209/20* (2006.01)

(52) U.S. Cl.
CPC .......... *B01J 19/122* (2013.01); *A61K 9/0085* (2013.01); *A61K 41/0042* (2013.01); *A61K 47/48023* (2013.01); *A61K 47/48061* (2013.01); *A61K 47/48246* (2013.01); *A61K 49/0021* (2013.01); *A61K 49/0032* (2013.01); *A61K 49/0052* (2013.01); *A61K 49/0056* (2013.01); *A61N 5/062* (2013.01); *C07C 59/66* (2013.01); *C07D 209/12* (2013.01); *C07D 209/20* (2013.01); *A61N 2005/0659* (2013.01)

(58) Field of Classification Search
CPC ......... A61K 41/00; A61K 47/48; A61K 49/00
See application file for complete search history.

(56) References Cited

U.S. PATENT DOCUMENTS

| | | | | |
|---|---|---|---|---|
| 5,998,580 | A * | 12/1999 | Fay | C07K 1/1077 436/518 |
| 6,274,086 | B1 | 8/2001 | Wilson et al. | |
| 7,449,277 | B2 | 11/2008 | Hatakeyama et al. | |
| 2005/0037401 | A1 | 2/2005 | Cammack et al. | |
| 2010/0035290 | A1 | 2/2010 | Sobek et al. | |
| 2011/0065040 | A1 | 3/2011 | Masuyama et al. | |

FOREIGN PATENT DOCUMENTS

| | | |
|---|---|---|
| JP | 2007114728 A | 5/2007 |
| JP | 2008304767 A | 12/2008 |
| WO | 99-10046 | 3/1999 |
| WO | 2010-039886 | 4/2010 |
| WO | 2011-057028 | 5/2011 |

OTHER PUBLICATIONS

Narayan, R.K., et al., "Clinical Trials in Head Injury" *J. Neurotrauma* May 2002; 19(5): 503-557.
Giza, C.C., et al al., "The Neurometabolic Cascade of Concussion" *Journal of Athletic Training* (2001) 36(3): 228-235.
Kochaneck, P.M., et al., "Guidelines for the Acute Medical Management of Severe Traumatic Brain Injury in Infants, Children, and Adolescents—Second Edition" *Pediatr Crit Care Med* (2012) vol. 13, No. 1 (Suppl.) S1-S82.
Yeung, J.K., et al., "A Review of Etomidate for Rapid Sequence Intubation in the Emergency Department" *Pharmacotherapy* May 2002; 4(3) 194-198.
Hatton, J., et al., "Dosing and Safety of Cyclosporine in Patients with Severe Brain Injury" *J. Neurosurg* Oct. 2008; 109(4) 699-707.
Bernaudin, M., et al., "A Potential Role for Erythropoietin in Focal Permanent Cerebral Ischemia in Mice" *Journal of Cerebral Blood Flow and Metabolism* (1999) 19; 643-651.
Readnower, R.D., et al., "Increase in Blood Brain Barrier Permeability, Oxidative Stress, and Activated Microglia in a Rat Model of Blast Induced Traumatic Brain Injury" *J Neurosci Res*. Dec. 2010; 88(16): 3530-3539.

(Continued)

*Primary Examiner* — Michael G. Hartley
*Assistant Examiner* — Jagadishwar Samala
(74) *Attorney, Agent, or Firm* — Steinfl + Bruno LLP

(57) ABSTRACT

Methods are described and related devices, compositions, and systems, in which a caged compound is administered to a biological environment, the caged compound being caged with a long wavelength absorber, the long wavelength being a wavelength greater than or equal to 750 nm; and irradiating the biological environment to excite the long wavelength absorber with light at a wavelength in a range from 900-1100 nm, thus decaging the compound.

7 Claims, 13 Drawing Sheets

(56) References Cited

OTHER PUBLICATIONS

Marion, D.W., et al., "Proceedings of the Military mTBI Diagnostics Workshop, St. Pete Beach, Aug. 2010" *Journal of Neurotrauama* 28:517-526 (Apr. 2011).

The Management of Concussion/mTBI Working Group "VA/DoD Clinical Practice Guideline for Management of Concussion/Mild Traumatic Brain Injury (mTBI)" Version 1.0—2009 (112 pgs).

Finkelstein, E.A., et al., "Incidence and Economic Burden of Injuries in the United States" *J Epidemiol Community Health* (2007) 61: 926-927.

Taylor, B.C., et al., "Prevalence and Costs of Co-Occurring Traumatic Brain Injury with and without Psychiatric Disturbance and Pain among Afghanistan and Iraq War Veteran VA Users" *Med Care.* 2012; 50(4):342-346.

Sinz, E.H., et al., "Inducible Nitric Oxide Synthase is an Endogenous Neuroprotectant after Traumatic Brain Injury in Rats and Mice" *The Journal of Clinical Investigation* Sep. 1999; vol. 104, No. 5; 647-656.

Shellington, D.K., et al., "Polynitroxlated Pegylated Hemoglobin: A Novel Neuroprotective Hemoglobin for Acute Volume-Limited Fluid Resuscitation after Combined Traumatic Brain Injury and Hemorrhagic Hypotension in Mice" *Crit Care Med.* Mar. 2011; 39(3): 494-505.

Williams, C., et al., "Transcriptome Analysis of Synaptoneurosomes Identifies Neuroplasticity Genes Overexpressed in Incipient Alzheimer's Disease" *PLoS ONE* Mar. 2009; vol. 4, Issue 3; e4936 (13 pages).

Meera, P., et al., "Etomidate, Propofol and the Neurosteroid THDOC Increase the GABA Efficacy of Recombinant $\alpha 4\beta 3\delta$ and $\alpha 4\beta 3$ $GABA_A$ Receptors Expressed in HEK Cells" *Neuropharmacology* Jan. 2009 56(1): 155-160.

Meera, P., et al., "Large Conductance voltage- and Calcium-Dependent $K^+$ Channel, a Distinct Member of Voltage-Dependent Ion Channels with Seven N-terminal Transmembrane Segments (S0-S6), an Extracellular N Terminus, and an Intracellular (S9-S10) C Terminus" *Proc. Natl. Acad. Sci. USA* vol. 94; Dec. 1997; 14066-14071.

Mordwinkin, N.M., et al., "Angiotensin-(1-7) Administration Reduces Oxidative Stress in Diabetic Bone Marrow" *Endocrinology* May 2012; 153(5); 2189-2197.

Bayir, H., et al., "Enhanced Oxidative Stress in iNOS-deficient Mice after Traumatic Brain Injury: Support for a Neuroprotective role of iNOS" *Journal of Cerebral Blood Flow & Metabolism* (2005) 25, 673-684.

Tehranian, R., et al., "Distribution of Bax Protein Prevents Neuronal Cell Death but Produces Cognitive Impairment in Mice following Traumatic Brain Injury" *Journal of Neurotrauma* Jul. 2008; 25:755-767.

Haselkorn, M.L., et al., "Adenosine $A_1$ Receptor Activation as a Brake on the Microglial Response after Experimental Traumatic Brain Injury in Mice" *Journal of Neurotrauma* 27: 901-910 May 2010.

International Search Report mailed on Mar. 29, 2013 for PCT/US2012/068626 filed in the name of California Institute of Technology et al.

Albensi, B.C., et al., "Cyclosporin Ameliorates Traumatic Brain-Injury-Induced Alterations of Hippocampal Synaptic Plasticity" *Experimental Neurology* 162, 385-389 (2000).

Corrigan, J.D., et al., "The Epidemiology of Traumatic Brain Injury" *J. Head Trauma Rehabil* vol. 25, No. 2, 72-80 (2010).

Sauaia, A., et al., "Epidemiology of Trauma Deaths: A Reassessment" *The Journal of Trauma: Injury, Infection, and Critical Care* (1995) vol. 38, No. 2; 185-193.

Granacher RP, "The Epidemiology and Pathophysiology of Traumatic Brain Injury" in *Traumatic Brain Injury: Methods for Clinical & Forensic Neuropsychiatric Assessment*, 2nd Ed. Boca Raton: CRC (2007) pp. 1-47. ISBN 0-8493-8138-X.

Martland H.S. "Punch Drunk" *Jour. A.M.A.* (1928); 91:1103-1107.

Plassman B.L., et al., "Documented head injury in early adulthood and risk of Alzheimer's disease and other dementias" *Neurology* (2000);55(8):1158-1166.

Lye, T.C., et al., "Traumatic brain injury as a risk factor for Alzheimer's disease: A review" *Neuropsych Rev* (2000)10(2); 115-129.

Garga N., et al., "Posttraumatic epilepsy: a major problem in desperate need of major advances" *Epilepsy Curr.* (2006) 6(1); 1-5.

Bower J.H., et al., "Head trauma preceding PD: a case-control study" *Neurology* (2003) 60(10):1610-1615.

Cohn B.F., et al., "Results of a feasibility trial to achieve total immobilization of patients in a neurosurgical intensive care unit with etomidate" *Anaesthesia* (1983) 38 Suppl:47-50.

Adnet F., et al., "A survey of sedation protocols used for emergency endotracheal intubation in poisoned patients in the French prehospital medical system" *European Journal of Emergency Medicine* 5: 415-419 (1988).

Murugaiah K.D. et al., "Effects of intravenous general anesthetics on [3H]GABA release from rat cortical synaptosomes" *Anesthesiology* 89(4): 919-928 (1998).

Watson J.C. et al., "An assessment of the cerebral protective effects of etomidate in a model of incomplete forebrain ischemia in the rat" *Neurosurgery* 30(4): 540-544 (1992).

Patel P.M., et al., "Etomidate reduces ischemia-induced glutamate release in the hippocampus in rats subjected to incomplete forebrain ischemia" *Anesth Analg* 80: 933-939 (1995).

Grasso, G., "Neuroprotective effect of recombinant human erythropoietin in experimental subarachnoid hemorrhage," *Journal of Neurosurgical Sciences*, vol. 45, No. 1, 7-14, (2001).

Morishita, E., et al., "Erythroproetin receptor is expressed in rat hippocampal and cerebral cortical neurons, and erythropoietin prevents in vitro glutamate-induced neuronal death," *Neuroscience* vol. 76, No. 1, 105-116 (1996).

Alafaci, C., et al., "Effect of recombinant human erythropoietin on cerebral ischemia following experimental subarachnoid hemorrhage," *European Journal of Pharmacology* vol. 406, No. 2, 219-225 (2000).

Marti, H.H., et al., "Detection of erythropoietin in human liquor: intrinsic erythropoietin production in the brain," *Kidney International* vol. 51, No. 2, 416-418, (1997).

Juul, S.E. et al., "Erythropoietin in the cerebrospinal fluid of neonates who sustained CNS injury" *Pediatric Research*, vol. 46, No. 5, 543-547 (1999).

DeWitt D.S., et al., "Blast-induced brain injury and posttraumatic hypotension and hypoxemia" *Neurotrauma* 26:877-889 (2009).

Hovda D.A., et al., "The neurochemical and metabolic cascade following brain injury: moving from animal models to man" *J Neurotrauma* (1995) vol. 12 No. 5; 903-906.

Jöbsis, F.F., Noninvasive, Infrared Monitoring of Cerebral and Myocardial Oxygen Sufficiency and Circulatory, Science, vol. 198 (1977) 1264-1267.

Tehranian R., et al., "Transgenic mice that overexpress the anti-apoptotic Bcl-2 protein have improved histological outcome but unchanged behavioral outcome after traumatic brain injury" *Brain Research* 26: 1101 (2006) 126-135.

Whalen M.J., et al., "Effect of Traumatic Brain Injury in Mice Deficient in Intercellular Adhesion Molecule-1: Assessment of Histopathologic and Functional Outcome" *Jouranl of Neurotrauma* 16(4): 299-309 (1999).

Foley L.M., et al., "Effect of inducible nitric oxide synthase on cerebral blood flow after experimental traumatic brain injury in mice" *Journal of Neurotrauma* 25:299-310 (2008).

Hendrich K.S., et al., "Cerebral perfusion during anesthesia with fentanyl isoflurane or pentobarbital in normal rats studied by arterial spin-labeled MRI" *Magnetic Resonance in Medicine* 46:202-206 (2001).

Kochanek P.M., et al., "Cerebral blood flow at one year after controlled cortical impact in rats: assessment by magnetic resonance imaging" *Journal of Neurotrauma* (2002) 19(9):1029-1039.

(56) References Cited

OTHER PUBLICATIONS

Blasiole B., et al., "100% Oxygen is beneficial during resuscitation of experimental combined traumatic brain injury and hemorrhagic shock in mice" *ATACCC Annual Meeting* Aug. 15-19, 2011 (1 page).

Manole M. et al., "Polynitroxil albumin and albumin therapy after pediatric asphyxial cardiac arrest: Effects on cerebral blood flow and neurological outcome" *Journal of Cerebral Blood Flow & Metabolism* (2012) 32, 560-569.

Coronado V.G., et al., "Epidemiology" in *Neurotrauma and Critical Care: Brain* New York, NY: Thieme; (2009): 3-19.

Faul M., et al., "Traumatic brain injury in the United States: emergency department visits, hospitalizations, and deaths, 2002-2006" Atlanta, GA: CDC, National Center for Injury Prevention and Control; (2010).

Agmon, N. et al. "Electronic determinants of photoacidity in cyanonaphthols" J. Am. Chem. Soc. 2002; vol. 124, No. 6; pp. 1089-1096.

Fabian, J. et al. "Near-Infrared Absorbing Dyes" Chem. Rev. 1992; vol. 92; pp. 1197-1226.

Gandolfi, C. et al. "N-Acyl-2-substituted-1,3-thiazolidines, a New Class of Non-narcotic Antitussive Agents: Studies Leading to the Discovery of Ethyl 2-[(2-Methoxyphenoxy)methyl]-B-oxothiazolidine-3-propanoate" J. Med. Chem. 1995; vol. 38, pp. 508-525.

Garman, R. et al. "Blast exposure injury in rats with body protection is characterized primarily by diffuse axonal injury" Journal of Neurotrama; 2011; vol. 28; pp. 947-959.

Gerowska, M. et al. "Efficient reverse click labeling of azide oligonucleotides with multiple alkynyl Cy-Dyes applied to the synthesis of HyBeacon probes for genetic analysis" Tetrahedron; 2012; vol. 68; pp. 857-864.

Greene, T., et al., "Protecting groups in organic synthesis". Wiley, New York. 1999. pp. 297-348.

IEC 60601-2-33 "Part 2-33: Particular Requirements for the Safety of magnetic resonance equipment for medical diagnosis" May 2002; $2^{nd}$ Edition; 11 pages.

Joullie, M. et al. "Evolution of amide bond formation" ARKIVOC; 2010; No. viii; pp. 189-250.

Lait, S. et al. "Synthesis of a 1,3-Spiro-amino-alcohol-derived chiral auxiliary and its application to Diels-Alder reactions" Tetrahedron: Asymmetry; 2003; pp. 749-756.

Lin, C.-H. et al. "Iterative synthesis of acenes via homo-elongation" ChemComm; 2009; pp. 803-805.

Mason, S. et al. "Solid-Phase Methods for the Synthesis of Cyanine Dyes" J. Org. Chem.; 2005; vol. 70; pp. 2939-2949.

Mishra, A. et al. "Cyanines during the 1990s: A Review" Chem. Rev.; 2000; vol. 100; pp. 1973-2011.

Niu, S. "Advanced water soluble BODIPY dyes: Synthesis and application" Thesis; University of Strasbourg; Jul. 2011; 182 pages.

Niu, S. et al. "Water-Soluble BODIPY Derivatives" Organic Letters; 2009; vol. 11; No. 10; pp. 2049-2052.

Oushiki, D. et al. "Near-Infrared Fluorescence Probes for Enzymes Based on Binding Affinity Modulation of Squarylium Dye Scaffold" Analytical Chemistry; 2012; vol. 84; pp. 4404-4410.

Pines, D. et al., "Solvent Assisted Photoacidity", in Handbook of Hydrogen Transfer, R.L. Schowen, Editor. 2006, Wiley-VCH: Weinheim, Germany. pp. 377-415.

Ranade, A. et al. "A facile synthesis of dihydronaphthopyrans" J. Chem. Research (S); 2003; pp. 461.

Shear, D. et al. "Severity Profile of Penetrating Ballistic-Like Brain Injury on Neurofunctional Outcome, Blood-Brain Barrier Permeability, and Brain Edema Formation" Journal of Neurotrauma; 2011; vol. 28; No. 10; pp. 2185-2195.

Tolbert, L. et al. "Excited-State Proton Transfer: From Constrained Systems to "Super" Photoacids to Superfast Proton Transfer" Acc. Chem. Res.; 2002; vol. 35; No. 1; pp. 19-27.

International Search Report for International Application No. PCT/US2012/068629 filed Dec. 7, 2012 on behalf of California Institute of Technology. Mail Date: Mar. 28, 2013. 4 pages.

Written Opinion for International Application No. PCT/US2012/068629 filed Dec. 7, 2012 on behalf of California Institute of Technology. Mail Date: Mar. 28, 2013. 4 pages.

\* cited by examiner

CAGED COMPOUND DELIVERY AND RELATED COMPOSITIONS, METHODS AND SYSTEMS

CROSS REFERENCE TO RELATED APPLICATIONS

The present application claims priority PCT Application No. PCT/US2012/068626, filed on Dec. 7, 2012, which claims priority to U.S. Provisional Application No. 61/568, 046, entitled "Long Wavelength activation of bioactive compound" filed on Dec. 7, 2011, and is related to PCT Application No. PCT/US2012/068629 entitled "Photoacid compounds, and related compositions methods and systems" filed on Dec. 7, 2012, each of which is incorporated herein by reference in its entirety.

FIELD

The present disclosure relates to compound delivery in a biological environment and in particular to caged compound delivery, and related compositions, methods and systems

BACKGROUND

Molecular delivery has been a challenge in the medical field as well as in the field of biological molecule analysis, in particular when aimed at obtaining controlled delivery of analytes of interest to specific environments. Whether for medical applications or for fundamental biology studies, several methods are commonly used for the delivery of various classes of biomaterials and biomolecules.

Controlled delivery of targets to specific environments, e.g. specific cell types and/or tissues of individuals in vitro and/or in vivo is currently still challenging, especially when directed at providing controlled release of the target in a controllable conformation, typically associated to a biological activity.

SUMMARY

Described herein are methods and systems for controlled delivery of compounds in a biological environment. In particular, in embodiments herein described controlled delivery of a compound of interest is performed by providing a compound of interest as a caged compound to a biological environment and then uncaging the caged compound through light irradiation at a suitable wavelength.

According to a first aspect, an embodiment describes the administering of a caged compound to a biological environment, the caged compound being caged with a long wavelength absorber, the long wavelength being a wavelength greater than or equal to about 750 nm; and irradiating the biological environment to excite the long wavelength absorber with light at a wavelength in a range from about 900 to about 1100 nm, thus decaging the compound.

According to a second aspect, an embodiment describes of a system for delivering caged compound to a biological environment the system comprising, a long wavelength absorber, a compound of interest, a light emitting device adapted to irradiate light and excite the long wavelength absorber at a wavelength of from about 900 nm to about 1100 nm for simultaneous combined or sequential use in a method of the disclosure.

According to a third aspect, an embodiment describes a wearable infrared-emitting device comprising: a support adapted to be worn, in use, on a body part of an individual; an array of infrared transmitters and infrared detectors arranged on the support, the infrared transmitters configured to emit infrared light at a wavelength in a 900-1,100 nanometer range, the infrared detectors configured to detect the infrared light transmitted through the individual's body part; and a control circuit to control duty cycle and time-gating of the array of the infrared transmitters, wherein the duty cycle and the time-gating are configured to trigger and release caged compound in the brain tissue.

Methods, systems and related devices herein described allow in some embodiments delivery of chemical compounds to biological environments in a controlled fashion possibly directed to targeted activation of compounds of interest following delivery.

Caged compounds and long wavelength absorbers and related methods and systems herein described can be used in connection with applications wherein controlled delivery of a compound of interest is desired. Exemplary applications includes application in medical, biological, chemical and pharmacological fields, wherein a controlled release of a compound of interested in a selected biological environment and/or verification and/or validation of a desired chemical biologica and/or pharmacologic activity (e.g. pharmacokinetics, pharmacodynamics, and tocicokinetics) for treatment, imaging or experimental purpose is desired.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 5 depicts approaches directed to identify caged compounds and related methods and systems for targeted delivery according to embodiments herein described. In particular.

DETAILED DESCRIPTION

Figure 1:
FIG. 1 shows a schematic illustration exemplifying a reaction scheme for the delivery of a caged drug compound linked to a Near Infrared Range (NIR) absorber.

Method and systems and related compositions and devices are described herein that allow delivery of a compound in a biological environment.

The term "compound" as used herein indicates chemical substance consisting of two or more different chemical elements linked by chemical bonds, that can be separated into simpler substances by chemical reactions. In compounds in the sense of the present disclosure the chemical bonds can be covalent bonds, ionic bonds, dipole-dipole interactions, London dispersion forces and hydrogen bonds. The compounds herein described are typically characterized by the ability to perform biological and/or chemical reactions of interest in a biological environment.

The wording "biological environment" as used herein indicates an environment comprising a cell and/or a cellular component. Biological environments in the sense of the present disclosure comprise in vitro biological environments such as cells derived from multicellular organisms (e.g. cell culture or tissue culture), subcellular components and/or organelles (e.g. mitochondria or ribosomes), cellular or subcellular extracts (e.g. wheat germ or reticulocyte extracts), or purified molecules in the test tube (e.g. proteins, DNA, or RNA, individually or in combination); ex vivo biological environments such as tissues or portion thereof, organs or portion thereof, biopsies, or cadavers or portion thereof; and "in vivo" biological environments such as living organisms, animals, or human patients. Exemplary biological environments in the sense of the present disclosure further comprise an aqueous solution of cellular proteins and organelles from a lysed cell, as well as a cell population immobilized on a solid surface or suspended in a culture a mass or population of cells forming a tissue or a portion thereof, an abnormal cellular growth, a tumor, a tissue and/or a body part or portion thereof and additional environment identifiable by a skilled person upon reading of the present disclosure.

In particular, in embodiments herein described a compound of interest is delivered to a biological environment as a caged compound. The term "cage" as used herein relates to the interaction between a first chemical moiety and a second chemical moiety that minimizes the participation in physical chemical or biological reactions of the second chemical moiety. In particular, caging can occur for example through binding of the first chemical moiety to the second chemical moiety through a chemical bond or physical containment of a second chemical moiety by a first chemical moiety (such as a carbon nanotube). Accordingly, a "caged compound" as used herein, relates to a chemical moiety in a cage interaction with another chemical moiety, and can be reversed by means suitable to modify the cage interaction and decage the second moiety. Exemplary means comprise a drug compound caged via a covalent bond to a separate molecule that is inert; when decaged, the drug compound becomes active and can participate in drug-related chemical reactions such as substrate binding or neuromodulation. The term "decage" or "uncage" but herein is defined as a modification of a caging interaction between a first and second chemical moiety to the chemical moiety, liberating the second molecule to participate in chemical or biological reactions. In particular, decaging can be performed through cleavage of a chemical bond, a stereochemical change of the caged compound or physical release of the caged compound. Decaging of a compound can be detected by identifying the decaged activity of the uncaged compound or by LC-MS spectroscopy to identify either the caged compound, the first moiety, or the second moiety (see Example 2).

In embodiments herein described the compound to be delivered is caged by a long wavelength absorber, which is a chemical moiety able to switch from a ground state to an excited state upon light irradiation at a long wavelength, (a wavelength greater than or equal to about 750 nm). The term "excited state" as used herein refers to an electronic state of a moiety in which the molecule has absorbed light energy and been promoted to a higher energy state. This process is referred to as "excitation." The term "ground state" refers to the electronic state of a moiety in which the electrons are in their lowest energy molecular orbitals. In photoacid compounds, the excitation can be accomplished, for example, by irradiating a photoacid molecule with light of energy equal to the difference in energy between the ground state and the excited state. The energy of the light is determined by the wavelength of the light according the relationship $E=hc/\lambda$, where E is the energy of the photon, h is Plank's constant, and $\lambda$ is the wavelength of the light. In particular, in some embodiments, the light used to effect the excitation is infrared or near infrared light.

The term "infrared light" as used herein refers to light in the infrared region of the electromagnetic spectrum from approximately 0.75 μm to approximately 1000 μm. The term "near infrared" refers to a region of the infrared spectrum from approximately 0.75 μm (750 nm) to approximately 1.4 μm (1400 nm).

In embodiments herein described the long wavelength absorber has a ground state at a condition compatible with viability of the cell and/or cell component in the biological environment of interest and is capable of assuming an excited state upon absorbance of the light at the long wavelength in the biological environment. In embodiments herein described, promotion from the ground state to a suitable excited state of the long wavelength absorber results in decaging of the compound of interest from the wavelength absorber, following a reaction also identified as photoionic decaging.

In some embodiments, a preparation of caged compounds herein described is designed to have a photoacid compound comprising a light absorbing moiety attaching a payload moiety through a linker moiety wherein the linker moiety is an organic moiety comprising a geminal dialkyl moiety linked to an ester group having a carbonyl oxygen, the carbonyl group of the ester attaching the payload moiety; the light absorbing moiety is an organic moiety attaching the linker moiety in ortho position to a hydroxyl group; and the linker is configured to present the carbonyl oxygen for reaction with the hydroxyl group.

In some embodiments, the light-absorbing moiety of a caged compound can be a substituted or unsubstituted polycyclic aromatic hydrocarbon or closed chain cyanine or hemicyanine and in particular substituted or unsubstituted naphthol.

In some embodiments, the linker moiety of the caged compound can be a monoalkoxy or a dialkoxy moiety in which the oxy group is linked to the ester group having the carbonyl oxygen.

In some embodiments, the payload moiety is a substituted or unsubstituted alkyl, aryl, heteroaryl, aminoalkyl, or oxyalkyl moiety.

In some embodiments, a preparation of caged compounds herein described is provided in which the linker moiety presents the carbonyl through an ester, and in particular a derivative of a t-butyl ester, a class that is especially sensitive to acid-catalyzed ester cleavage.

In some embodiments, a preparation of caged compounds herein described in which the cleavage process releases a generic entity $R_3CO_2H$, a carboxylic acid in which R3 is the compound of interested to be delivered.

In particular, in embodiments herein described photoacid compound herein described are substituted to present hydrophilic substituents (e.g. sulfonate, and in particular polysulfonates such as polysulfonate peptides or oligopeptides, as well as polyethylene glycol groups). In some embodiments water solubility can be imparted by a hydrophilic payload or suitable substituents comprised in the payload to achieve water solubility.

In particular, in some embodiments, a photoacid herein described has of the general structure according to formula (I):

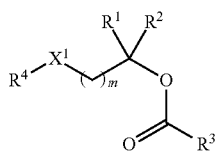

(I)

wherein:
R$^4$ is a light-absorbing moiety presenting a hydroxyl group for interaction with the carbonyl oxygen of the R$^3$(CO)O group, wherein the light-absorbing moiety is a substituted or unsubstituted polycyclic aromatic hydrocarbon, a substituted or unsubstituted closed chain cyanine, or a substituted or unsubstituted hemicyanine, and wherein the hydroxyl group is covalently bonded to the polycyclic aromatic hydrocarbon, the closed chain cyanine, or the hemicyanine, and the hydroxyl group is in a position ortho to X$^1$;
R$^3$ is a payload moiety, wherein the payload moiety is a substituted or unsubstituted alkyl, aryl, heteroaryl, alkoxy, alkylamino, or dialkylamino moiety; and
X$^1$ is independently selected from the group consisting of C and O;

m is between 0 and 3; and
R$^1$ and R$^2$ are independently $C_1$-$C_6$ alkyl groups, cycloalkyl, or substituted or unsubstituted hydrocarbylene groups wherein when R$^1$ and R$^2$ are substituted or unsubstituted hydrocarbylene groups they are linked together to form a cyclic moiety.

In particular, in the photoacid compound of formula (I) and other embodiments herein described, the moiety

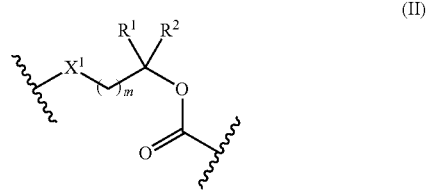

(II)

is the linker.

In particular, in some embodiments, R$^4$ can be a moiety of Formula (III):

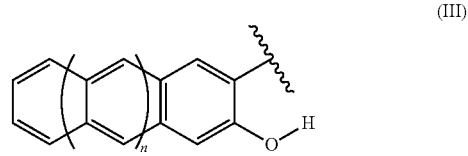

(III)

wherein n is between 0 and 5.

In particular, in some, R$^4$ can be a moiety of Formula (IV):

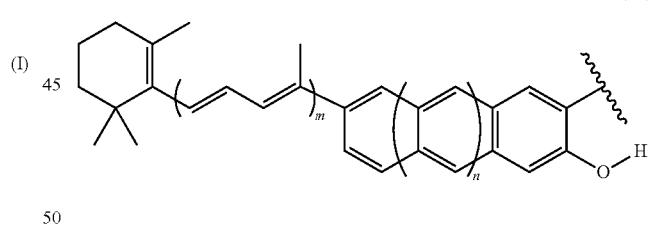

(IV)

where n is between 0 and 5, and m is between 1 and 3.

In particular, in some embodiments, R$^4$ can be a moiety of Formula (V):

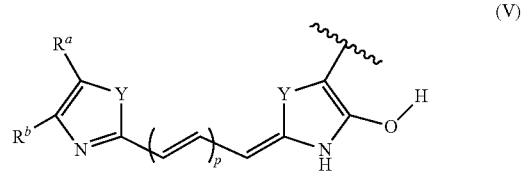

(V)

wherein R$^a$ and R$^b$ are independently H, alkyl, or O-alkyl; Y is N, O, or S; and p is between 1 and 4.

In particular, in some embodiments, $R^4$ can be a moiety of Formula (VI):

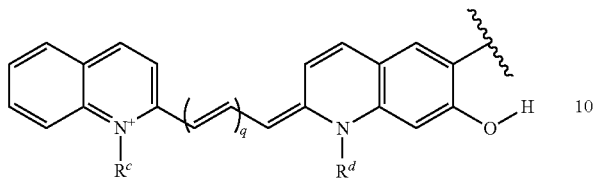
(VI)

wherein $R^c$ and $R^d$ are independently alkyl and q is between 1 and 4.

In particular, in some embodiments, $R^4$ can be a moiety of Formula (VII):

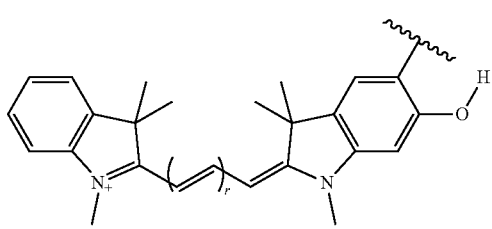
(VII)

wherein r is between 1 and 4.

In particular, in some embodiments, $R^4$ can be a moiety of Formula (VIII):

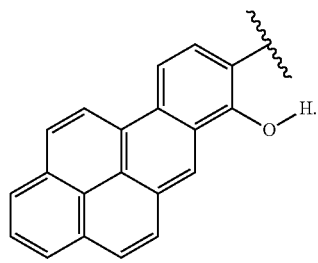
(VIII)

A skilled person will understand, upon a reading of the present disclosure, that the light absorbing moiety and herein described can be substituted or unsubstituted and in particular have additional substituents which can be added to impart additional functionalities such as, for example, hydrophilic substituents (e.g. sulfonate, and in particular polysulfonates such as polysulfonate peptides or oligopeptides, as well as polyethylene glycol groups), and functional groups and/or moieties to connect the photoacid compounds herein described to other molecules and/or substances (e.g. for connection to carbon nanotubes, fullerenes, antibodies, polymers, proteins, lipids, carbohydrates, and others identifiable to a skilled person).

In embodiments herein described wherein the caged compound is caged within a photoacid the caged compound can be comprised as a payload $R^3$ in a photoacid of Formula (I).

In particular, $R^3$ can be an organic moiety such as, for example a substituted or unsubstituted alkyl, aryl, heteroaryl, alkoxy, alkylamino, or dialkylamino moiety. In some embodiments, and in particular in embodiments where $R^3$ is a substituted or unsubstituted alkyl, aryl, heteroaryl molecule, $R^3$ is adapted to exist in a carboxylic acid form wherein the carboxylic acid form can be used to provide the carbonyl group of the linker of Formula (II).

In particular, in some embodiments, $R^3$ can be a moiety of Formula (IX):

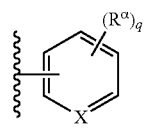
(IX)

wherein q is between 0 and 5, $R^\alpha$ is H, or substituted or unsubstituted alkyl, alkylamino, alkoxy, aryl, arylamino, aryloxy, heteroaryl, hetroarylamino, and heteroaryloxy; X is C or N; and wherein when q is greater than 1, each $R^\alpha$ is independent of the other $R^\alpha$ substituents.

In particular, in some embodiments wherein $R^3$ is according to Formula (IX), $R^3$ can be selected from the group consisting of Formulas (X)-(XII):

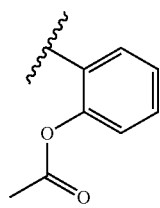
X

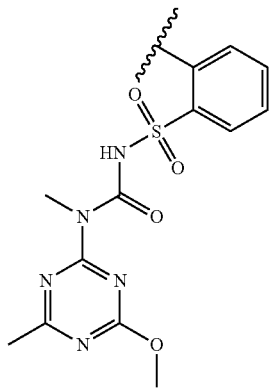
XI

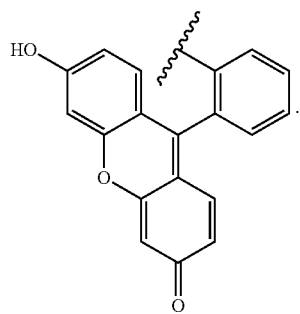
(XII)

In particular, in some embodiments, R³ can be a moiety of Formula (XIII):

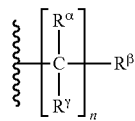

(XIII)

wherein n is between 1 and 5, $R^\alpha$, $R^\beta$, and $R^\gamma$ are independently H, or substituted or unsubstituted alkyl, alkylamino, alkoxy, aryl, arylamino, aryloxy, heteroaryl, hetroarylamino, and heteroaryloxy; and wherein when n is greater than 1, the $R^\alpha$ and $R^\beta$ of each $C(R^\alpha)(R^\beta)$ unit are independent of the $R^\alpha$ and $R^\beta$ of the other units.

In particular, in some embodiments wherein R³ is according to Formula (XIII), R³ can be selected from the group consisting of Formulas (XIV) and (XV):

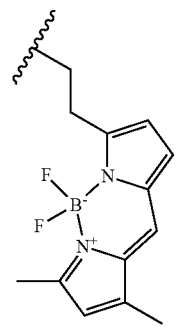

(XIV)

(XV)

In particular, in some embodiments, R³ can be a moiety of Formula (XVI):

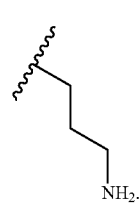

(XVI)

wherein p is between 1 and 5, $R^\alpha$, $R^\beta$, and $R^\gamma$ are independently H, or substituted or unsubstituted alkyl, alkylamino, alkoxy, aryl, arylamino, aryloxy, heteroaryl, hetroarylamino, and heteroaryloxy; wherein $R^\delta$ is H, substituted or unsubstituted alkyl, acyl, aryl; and wherein when p is greater than 1, the $R^\alpha$ and $R^\beta$ of each $C(R^\alpha)(R^\beta)$ unit are independent of the $R^\alpha$ and $R^\beta$ of the other units.

In particular, in some embodiments wherein R³ is according to Formula (XVI), R³ can be of Formula (XVII):

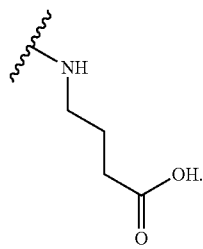

(XVII)

In particular, in some embodiments wherein R³ is according to Formula (XVI) and $R^\delta$ is acyl, R³ can be a peptide or oligopeptide such that the peptide or oligopeptide is attached to the linker via the N-terminus of the peptide or oligopeptide.

In particular, in some embodiments, R³ can be a moiety of Formula (XVIII):

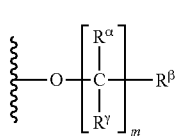

(XVIII)

wherein m is between 1 and 5, $R^\alpha$, $R^\beta$, and $R^\gamma$ are independently H, or substituted or unsubstituted alkyl, alkylamino, alkoxy, aryl, arylamino, aryloxy, heteroaryl, hetroarylamino, and heteroaryloxy; and wherein when m is greater than 1, the $R^\alpha$ and $R^\beta$ of each $C(R^\alpha)(R^\beta)$ unit are independent of the $R^\alpha$ and $R^\beta$ of the other units.

In particular, in some embodiments, R³ can be a moiety of Formula (XIX):

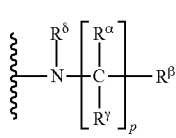

(XIX)

wherein q is between 0 and 4, $R^\alpha$ is H, or substituted or unsubstituted alkyl, alkylamino, alkoxy, aryl, arylamino, aryloxy, heteroaryl, hetroarylamino, and heteroaryloxy; ε is a substituted or unsubstituted hydrocarbylene, X is C or N; and wherein when q is greater than 1, each $R^\alpha$ is independent of the other $R^\alpha$ substituents.

In embodiments, of methods and systems herein described the administered compound is uncaged by irradiating the biological environment at a wavelength suitable to excite the light absorbing moiety of the photoacids herein described thus triggering the acid base reaction between the hydroxyl group of the light absorbing moiety and the carbonyl group of the linker thus releasing and therefore uncaging the compound (see Example 1). The term "irradiate" or "illuminate" as used herein relates to the exposure of the target compound and minimal surrounding area to appropriate levels of radiation, in the form of emitting light to result in a desired wavelength in the biological environment where caged compound is to located and intended to be released.

In some embodiments, suitable wavelength ranges can be determined based on the features of the biological environment that is targeted. For example in applications where irradiation of a brain portion located 4-6 cm into the brain across an intact skull is desired a suitable light radiation can be set at a wavelength between about 900 nm to about 1100 nm. Other suitable wavelengths can be identified by a skilled person in view of the distance and light scattering between the light source and the biological environment to be targeted, as well as physical chemical and biological features of the biological environment that affect light diffusion through the biological environment.

In some embodiments, in methods and systems herein described administering of a caged compound to a biological environment, is performed with a caged compound caged with a long wavelength absorber, where the long wavelength is a wavelength greater than or equal to about 750 nm.

In particular the administering can be performed according to techniques and procedures that are identifiable by a skilled person based on the targeted biological environment, desired amount of compound of interest to be administered and uncaged as well as the experimental design and/or conditions of choice which are functional to the desired amount and chemical and/or biological properties of a caged compound to be delivered.

For example, in embodiments, wherein the biological environment is in vitro, administering of the caged compound can be performed by providing the caged compound to the media surrounding the biological environment in a suitable amount and using additional techniques and approaches identifiable by a skilled person.

In embodiments, wherein the biological environment comprises an ex vivo specimen administering the caged compound can be performed by providing the caged compound in a suitable formulation to be administered using routes which can be identified by a skilled person based on the specific specimen at issue.

In embodiments herein described where the administering is performed in an individual in vivo, the administering can be performed by systemic and/or topical administration.

The wording "systemic administration" as used herein indicates a route of administration by which a caged compound is brought in contact with the body of the individual, so that the desired effect is systemic (i.e. non limited to the specific tissue where the chemical and/or biological activity of the caged compound is desired). The term "individual" as used herein in the context of treatment includes a single biological organism, including but not limited to, animals and in particular higher animals and in particular vertebrates such as mammals and in particular human beings. The wording "topical administration" as used herein indicates a route of administration by which a caged compound is brought in contact with the specific tissue or other biological environment where the chemical and/or biological activity of the caged compound is desired.

Exemplary systemic administration routes include enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion. In some embodiments, administration can be performed intravenously by introducing a liquid formulation including a caged compound in a vein of an individual using intravenous access methods identifiable by a skilled person, including access through the skin into a peripheral vein. In some embodiments, administration of a caged compound can be performed intraperitoneally, by injecting a caged compound in the peritoneum of an individual, and in particular of animals or humans. Intraperitoneal administration is generally preferred when large amounts of blood replacement fluids are needed, or when low blood pressure or other problems prevent the use of a suitable blood vessel for intravenous injection. In some embodiments administration can be performed intragastrically, including administration through a feeding tube. In some embodiments, administration of a caged compound can be performed intracranially.

In some embodiments a caged compound can be administered topically by applying the caged compound usually included in an appropriate formulation directly where its action is desired. Topical administration include but is not limited to epicutaneous administration, inhalational administration (e.g. in asthma medications), enema, eye drops (E.G. onto the conjunctiva), ear drops, intranasal route (e.g. decongestant nasal sprays), and vaginal administration.

For example, in embodiments wherein the biological environment is a body organ, of an individual administering can be performed by injection or ingestion designed for delivery a desired amount in the organ to be targeted. In embodiments wherein the biological environment is skin, administration can be performed injection or topical absorption. In embodiments wherein the biological environment is central nervous system of an individual, administration can be performed by injection or ingestion. In embodiments wherein the biological environment is a lung, administration can be performed by inhalation or injection. In some embodiments, wherein the biological environment is an eye, administration of the caged compound can be performed through topical absorption of drops or direct intraocular injection. In some embodiments, the biological environment comprises a retinal ganglion cells and the administering can be performed injection. In this embodiment, the compound can be injected intraocularly into the vitreous cavity targeting retinal ganglion. In some embodiments, the biological environment is a brain and the administering can be performed by injection or ingestion (see Example 3).

In methods and systems herein described the administered compound can then be uncaged by irradiating the biological environment comprising the caged compound to excite the long wavelength absorber within the biological environment with light at a wavelength in a range from about 900 to about 1100 nm, thus decaging the compound.

Figure 11:
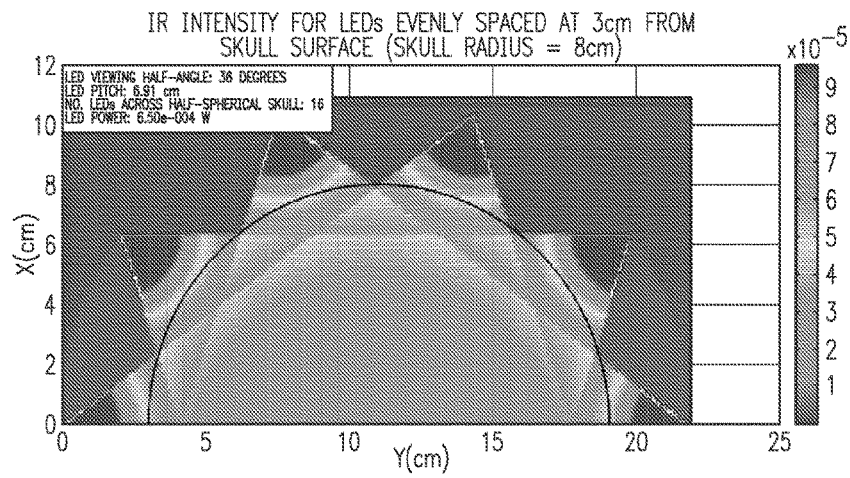
FIG. 11 shows a simulated EM field intensity from an array of LED (half circle outline shows skull) resulting from preliminary 2D EM simulations
Figure 12:
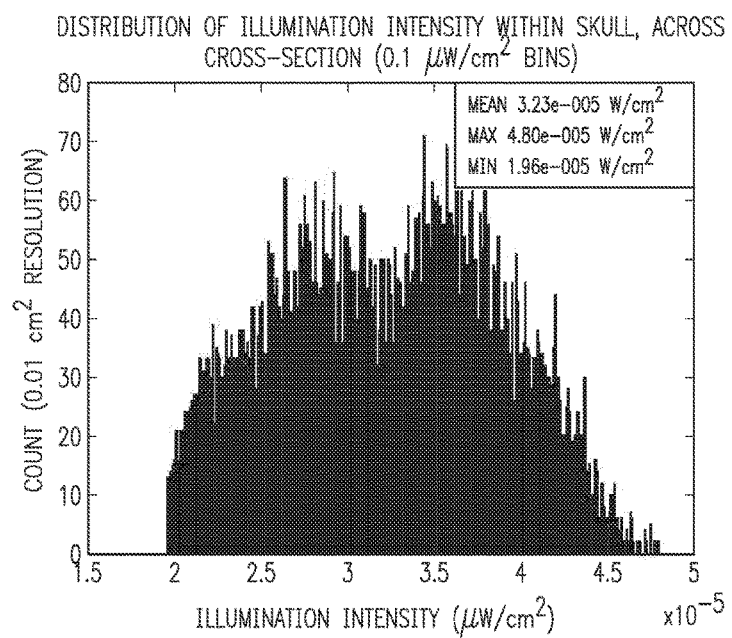
FIG. 12 shows illumination intensity across cross-section of skull resulting from preliminary 2D EM simulations

In some embodiments, the irradiating can be performed from a light source that is configured to excite the long wavelength absorber of the caged compound of interest possibly preceded by determining the related parameters which vary in view of the specific light source used and are identifiable by a skilled person upon reading of the present disclosure. For example, in an embodiment wherein the light source is an LED array, parameters include: number of LEDs, power per LED, the distance of the array from the biological environment, separation between LEDs, and LED/lens viewing half angle In some embodiments, irradiation parameters such as distance, intensity, and continuity of irradiation, con be predetermined in view of the specific biological environment to be irradiated according to techniques and approaches identifiable by a skilled person. For example, predetermination can be performed by thermoacoustic, photoacoustic imaging, or by availably known near infrared (NIR) windows based on known absorption coefficients and/or absorption coefficient spectrums. Thermoacoustic imaging can be performed for example by a device delivering electromagnetic radiation to the biological environment and an acoustic detector placed to the outside surface to measure the strength of the thermoacoustic waves. Photoacoustic imaging can be performed for example by a device delivering electromagnetic radiation to the biological environment and an ultrasonic detector placed to the outside surface to measure the strength of the ultrasonic emission. In addition, the molar extinction coefficient of deoxyhemoglobin has its highest absorption peak at 420 nm and a second peak at 580 nm, and its spectrum then gradually decreases as light wavelength increases. Oxyhemoglobin shows its highest absorption peak at 410 nm, and two secondary peaks at about 550 nm and about 600 nm. The absorption spectrum of water can be in the range from about 250 to about 1000 nm. The absorption spectrum for arteries ($SaO_2 \approx 98\%$) has $\lambda_{min}$ of about 686 nm and NIR window has a range of about 634-about 756 nm. The absorption spectrum for veins ($SvO_2 \approx 60\%$) has $\lambda_{min}$ of 730 nm and a NIR window of about 664-about 934 nm. The absorption spectrum for brain tissue ($StO_2 \approx 70\%$). $\lambda_{min}$=about 730 nm and a NIR window of about 656-about 916 nm. Infrared illumination between 900-1100 nm wavelength has depth of penetration of 4-6 cm into the brain across an intact skull (FIG. 11 and FIG. 12).

In some embodiments, the parameters for irradiation necessary from the light source to excite a long wavelength absorber to perform the chemical change can be determined by a skilled person in a laboratory setting for example by exposing the compound to a one or more wavelength and then detecting presence of an excited long wavelength absorber through techniques such as liquid chromatography-mass spectrometry (LC-MS), infrared (IR), nuclear magnetic (NMR) spectroscopy and additional techniques identifiable by a skilled person. Alternatively, or in addition, the skilled person can determine the irradiation associated to a desired delivery of a compound of interest by caging the long wavelength absorber to a compound, irradiating the resulting caged compound at one or more settings and detecting presence of a decaged compound in the one or more settings to identify a setting wherein a desired presence of the compound of interest is detected. Samples that contain the caged compound, the decaged compound, and the long wavelength absorber, can be for example collected and analyzed through LC-MS, IR, or NMR spectroscopy (see Example 2). In some embodiments, detection of decaging can be performed by labeling the caged compound with a suitable label configured to emit a labeling signal upon decaging of the compound.

The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

For example, in some embodiments the caged compound can be labeled with fluorescent/color-indicating molecule that only fluoresces/changes color when decaged and detectable fluorescence/color change is a positive indicator which wavelength is necessary to excite the long wavelength absorber. As a result, the fluorescence can be identified either through fluorescence microscopy or spectroscopy.

In some embodiments, in vitro experiments of the long wavelength absorber or the caged compound can be performed to identify wavelengths and/or settings for a desired in vitro biological environment and/or preliminary data directed to prepare in vivo experiments and in particular to minimize experimentation in the in vivo model. In an in vivo animal model experiment, a skilled person can use a light source as previously described (e.g., IR LED, an LCD panel, and additional sources identifiable by a skilled person) to irradiate animals that contain an administered compound caged by a long wavelength absorber. Based on data from corresponding in vitro experiments, the skilled person can adjust the specific parameters (e.g. distance and power) necessary for a long wavelength absorber to be excited by tracking the activity of the liberated uncaged compound (e.g. fluorescence, downstream drug effects, side-effects, death) or mass spectroscopic analysis of samples collected. For use on tissue and cell types in the body, a skilled person is aware of the different unique light absorption characteristics known in the medical community. A skilled person can empirically determine light absorption for example by placing probes (e.g., an optical probe for collecting returned light, or other device capable of same) at different sites of the tissue or body part; the probes at the cite measure and read out the wavelength absorbed when exposed to light in the location where the probe is placed. After determining the setting necessary for irradiation based on probe read outs, the skilled person is able to validate decaging from the irradiation from by tracking the activity of the liberated uncaged compound (e.g. fluorescence, downstream drug effects, side-effects, and death) or be mass spectroscopy sample analysis when available.

In some embodiments, the skilled person can adjust the distance of the light source to the target in conjunction with changes to the power settings of the light source. In embodiments, when the distance of the light source is not fixed, separate measurements for the power of irradiation can be made for each tested range of distance related to the specific long wavelength absorber used. In embodiments, when the distance of the light source is fixed, measurements for the power of irradiation are only for that range and directly related to the specific long wavelength absorber used. These experiments are typically done first in vitro, followed by non-human in vivo samples, and then ex vivo samples (see Examples 2, 3, 4). Experiments with varying distances and power of the light source irradiating human patients are performed in clinical trials under strict regulation and oversight. After clinical trials determine safe conditions, irradiation settings coupled with administering the caged compound is ready for general use.

In some embodiments, the particular wavelength range is known not to produce reactive oxygen species in biological environments.

In some embodiments, the irradiating can be performed following the administering of the caged compound at a time that is dependent on a window of time for a caged compound to reach a specific area of the biological environment from administration and for its clearance (through means not limited to diffusion, transport, secretion, or metabolic changes) in order to couple control release via irradiation. In some of those embodiments the window of time can be determined based on the feature of the biological environment at issue, for example in an in vitro environment of cell components, in which there is instantaneous entry and no exit for the compound upon administration the window of time is dependent on parameters such as solubility and coefficient of diffusion of the caged compound in the colture media, amount administered and additional parameters identifiable by a skilled person. In an in vivo biological environment wherein the administering is performed systemically to an individual, additional factors can also be taken into account including, clearance time (e.g. through metabolism and/or secretion), cell uptake and blood flow as well as additional parameters identifiable by a skilled person. In an in vitro environment of cell lines or an in vivo environment comprising of microorganisms, the window of time can be empirically determined by performing cell uptake assays with labeled substrates, LC-MS assays, and/or metabolite assays (see Example 2).

In some embodiments, where the biological environment is formed by in vivo or ex vivo environments larger than microorganisms, a window of time between administering and irradiating can be identified by pharmacokinetic approaches identifiable by a skilled person, which can be performed for example to establish a desired time for a compound to be absorbed, distributed, and eliminated or clearance (through metabolism or secretion) in the biological environment (see Example 2, Example 3, and Example 4). In particular, absorption refers to the ability and process of a dosage reaching the bloodstream and the related time can be measured according to approaches identifiable by a skilled person. For example compounds administered intravenously typically do not require absorption since they immediately reach the vascular system. Absorption can be for example determined by in vitro models such as membrane-based models (PAMPA), cell culture-based models (Caco-2), and transporter assays. Determining distribution of a compound can be performed by calculating the volume in which the drug is distributed is a product of the drug's dose divided by the plasma concentration ((Vd)=dose/plasma concentration) which is dependent on half-life of the compound. The half-life of the compound can be determined by in vitro systems to mimic the in vivo environments such as hepatocyte uptake assays or commercially available microsome systems utilizing cytochrome P450 enzymes.

In vitro half-life ($t_{1/2}$) can be determined using the equation: $t_{1/2} = \ln 2/(-k)$, where k represents the terminal elimination rate constant and is calculated as the negative slope of the line defined by the linear regression of the natural log loss of compound and incubation time. Clearance is defined as the volume of fluid that is completely cleared of the compound per unit time. Determining clearance of a compound can be performed by calculating the extraction ratio, blood (or serum) flow rates, solubility, and compute aggregation determined by in vitro systems to mimic the in vivo environments such as for example human cryopreserved hepatocytes or liver microsomes of the biological environment. Extraction ratios are calculated as the difference arterial compound concentration and venous drug concentration to the arterial compound concentration at the organ outflow. Flow rates can be calculated by blood pressure measurements. Solubility and compound aggregation is determined by flow cytometry analysis. Flow cytometry analysis can be performed by adding the compound to biological buffers that mimic the biological environment and measuring the particle size distribution with a flow cytometer.

Figure 7A:
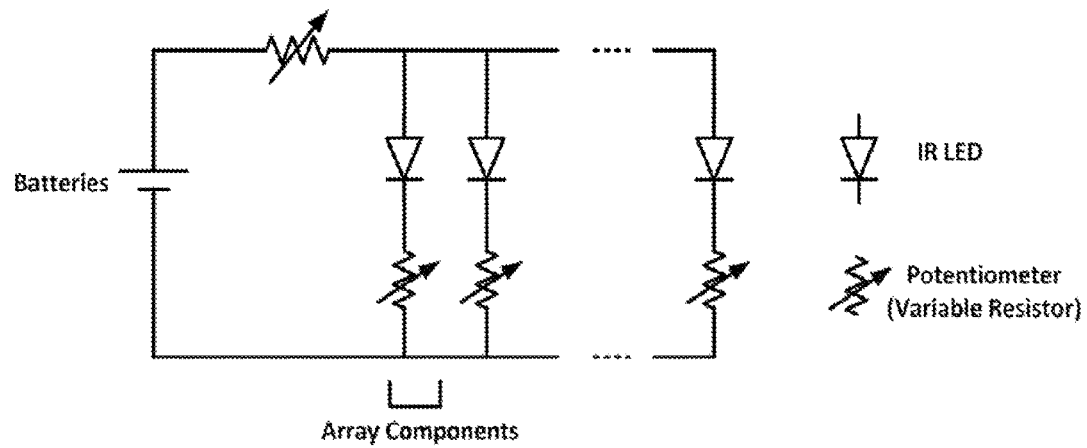
FIGS. 7A and 7B exemplify circuits designed to emit near infrared wavelength, the circuits comprising infrared LEDs and potentiometers. The arrangement in FIG. 7B allows for adjustment of LED parameters (e.g., power output).
Figure 7B:
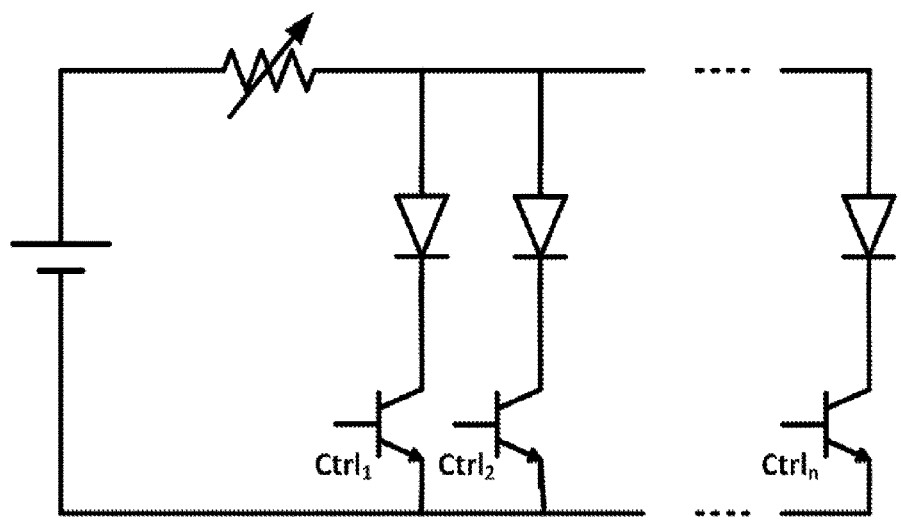

In some embodiments, light is emitted through a light source under conditions that irradiate a biological environment to produce a set, known, and consistent wavelength, known or predetermined in view of the specific environment, the desired effect and the conditions of choice as will be understood by a skilled person. For example, in some embodiments, the light source is selected to irradiate at levels that do not change the physical nature of the biological environment while in other embodiments the light source is selected to physically alters the biological environment (e.g. by melting or excision) in accordance with the specific biological environment and the experimental design as will be understood by a skilled person. Similarly, in some embodiments, the light source can irradiate the biological environment in pulses, and in other embodiments, the light source irradiates in a continuous fashion in accordance with the amounts, timing and location of the caged compound that is intended to be released. Exemplary light sources for this purpose are light emitting diodes, or LEDs, which are capable of delivering a controlled and set desired wavelength in the range indicated (e.g., 900 nm to 1100 nm) within the biological environment of the practitioner's choice. Exemplary circuit designs to emit near infrared wavelength are depicted in FIGS. 7A and 7B.

In some embodiments, a light source is a lamp, LCD panel, or LED display which is comprised of a non-portable device or a portable device. In some embodiments, the non-portable device or portable device containing the light source is a microscope, endoscope, flashlights, garments (see FIG. 6), or glasses. The non-portable or portable device comprising light sources, in some embodiments, also comprises image intensifier to further increase the emitted power from such devices in order to activate the preparation of molecules. Turning now to the description of FIG. 6, a wearable ultra-low weight, low power, time-gated, wearable infrared LED grid emitter (600), (610) is shown that transmits the energy deep into the brain across an intact skull, scalp and hair and triggers the release of caged compounds.

The LED emitter system according to the present disclosure uses longer wavelengths (900-1100 nm) and therefore reduces absorption and scattering of the energy, resulting in deeper light penetration into brain tissue (4-6 cm). FIGS. 7A and 7B show an exemplary arrangement of and array of infrared LEDs, each LED in series with a corresponding variable resistor. Alternatively, each LED can be put in series with a related transistor, as shown in FIG. 7B, each transistor being controlled by a dedicated control signal ctrl1, ctrl2, . . . Ctrln.

Figure 9:
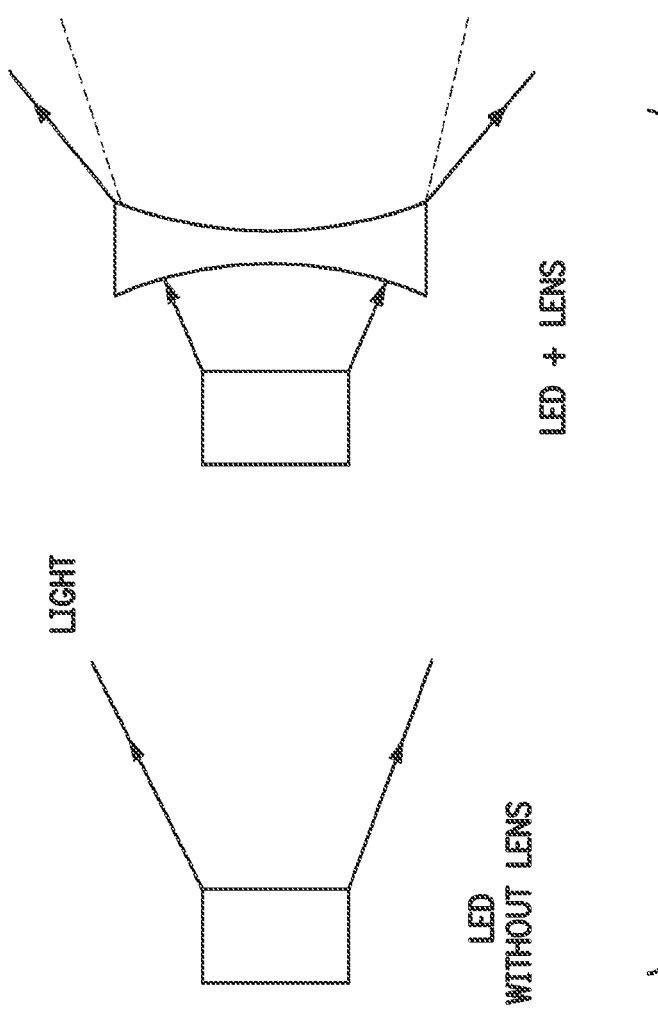
FIG. 9 shows an embodiment where both LEDs and lenses are provided, and in particular how a lens placed in front of an LED alters the behavior of transmitted light.

According to some embodiments of the present disclosure, the grid comprises a lensing arrangement that provides a more efficient energy delivery and allows reduction in the number of LED's. Reference can be made, for example, to FIG. 9 which shows an improved light distribution angle in presence of a lens (e.g. a bi-concave lens, as shown in the figure).

Figure 8:
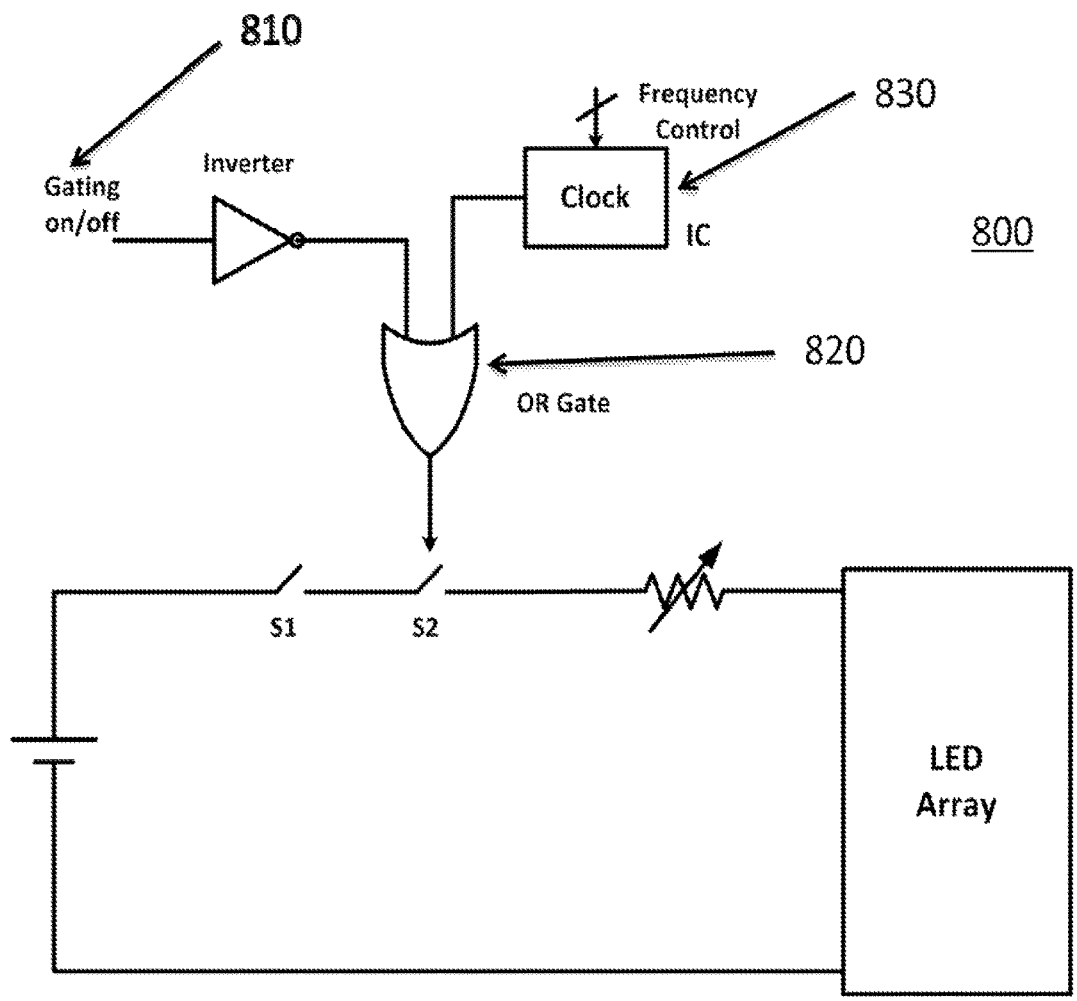
FIG. 8 shows an exemplary circuital arrangement for switching and gating of infrared LEDs as transmitters

The LED and associated systems are configured such that the duty cycle and time-gated functions trigger and release preferentially the caged-drug in brain tissue but not inside brain vessels. In order to do so, a circuit (800) like the one shown in FIG. 8 can be provided where, upon switching on of a general switch S1 and a switch S2, the latter being triggered either by a gating signal (810) or (820) by a clock circuit (830). Therefore, the LED array (840) is powered only when both switches S1 and S2 are on.

Figure 6A:
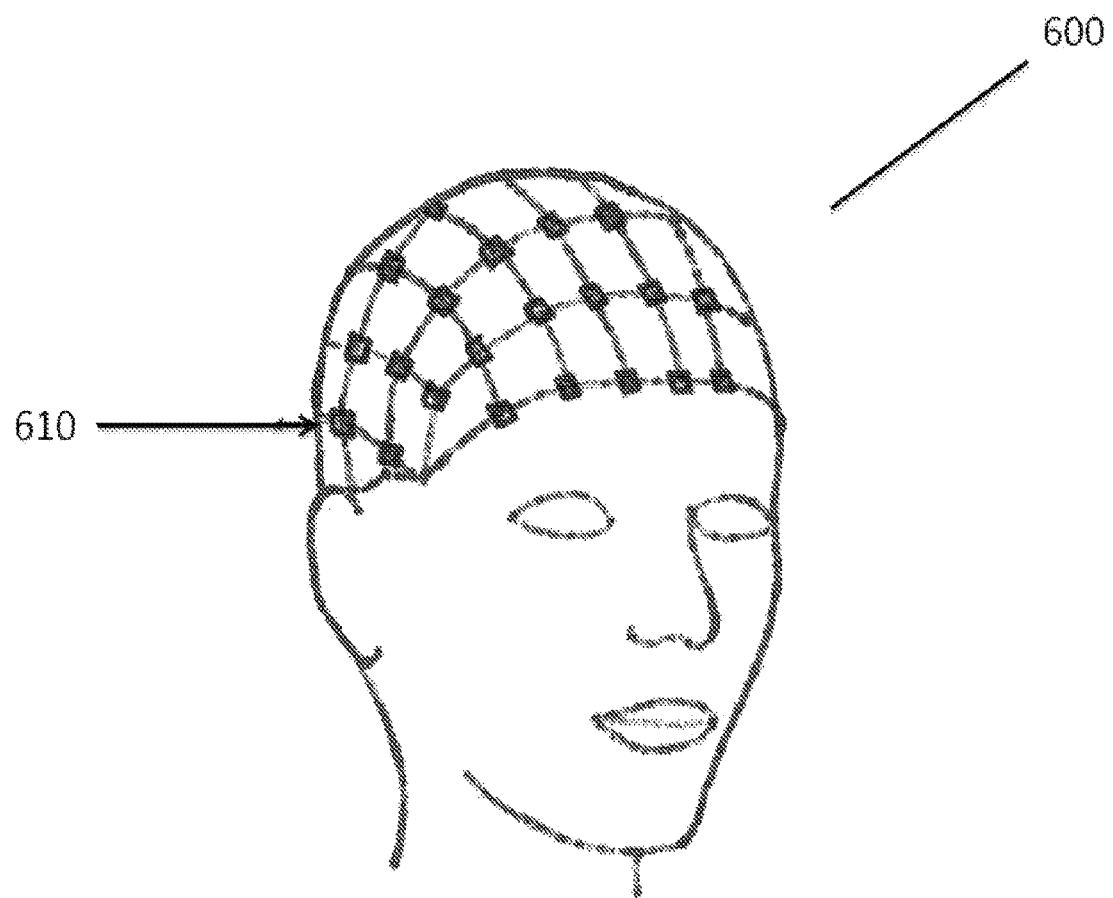
FIG. 6A shows a plurality/array of infrared (IR) transmitters and IR detectors arranged as a grid on a patient's head.
Figure 6B:
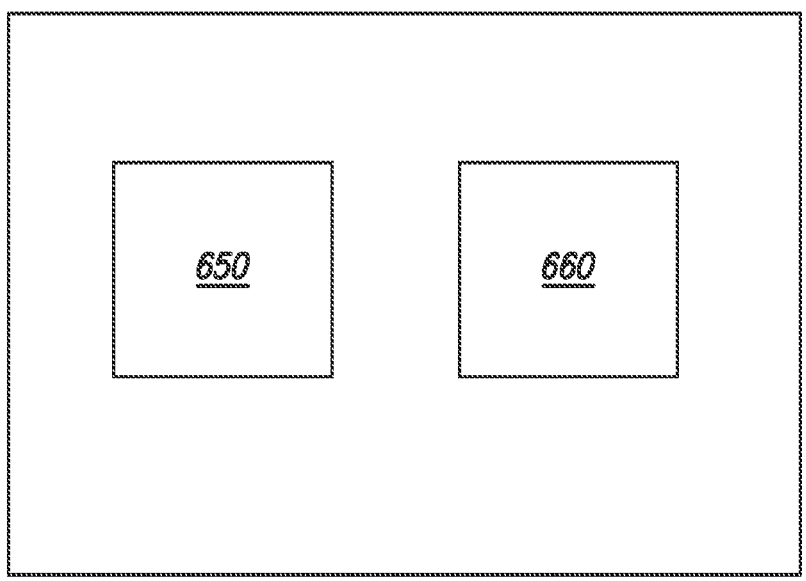
FIG. 6B shows a possible modular configuration of the IR transmitters and detectors of FIG. 6A, each module corresponding an IR transmitter and an IR detector.
Figure 10:
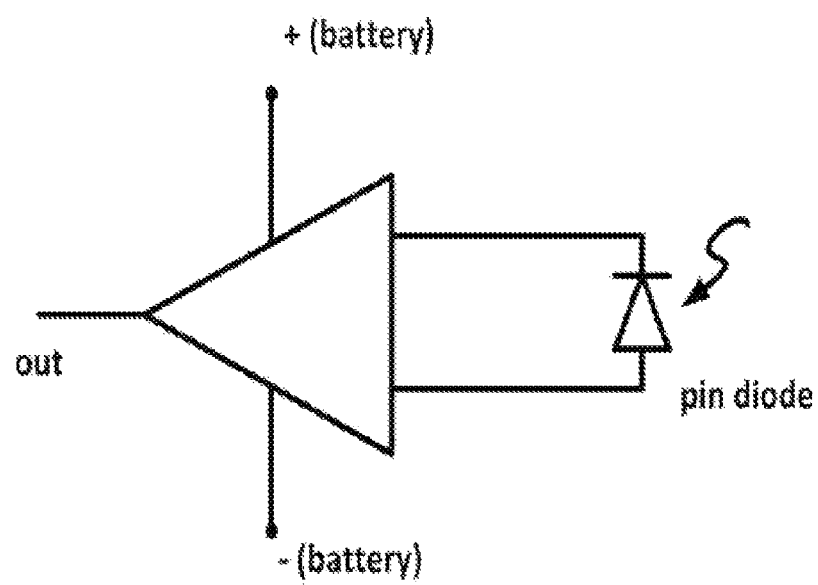
FIG. 10 exemplifies the electrical configuration of an infrared detector capable of collecting backscatter from LED emitters.

Turning now to the representation of FIG. 6A, each module (610) comprises an infrared transmitter section (650) and an infrared detector (660) section, as better shown in FIG. 6B. The infrared transmitter section (650) comprises, for example, an array of infrared LEDs like those shown in FIGS. 7A and 7B with associated variable resistors or transistors and one or more lenses like those shown in FIG. 9. On the other hand, a possible embodiment of the infrared detector section (660) of FIG. 6B is shown in FIG. 10, where the infrared detector section is configured as a PIN photodiode-transimpedance amplifier (TIA) detection module (1000), comprised of a PIN photodiode (1010) and a transimpedance amplifier (1020). Each detector section (660) of a module (610) is expected to allow detection of a transmission signal sent intracranially from the transmitter section (650) of a module (610) located on an opposite side of the head of the patient.

According to several embodiments of the present disclosure, the circuits employed in the above described device can be designed to require ultra-low power and dissipate little to no heat. By way of example, the LED array can be driven using two small lithium ion batteries with protection circuitry. Additionally, the LED array can be designed to operate in a range such that the maximal permissible temperature rise does not exceed 1° C. above body temperature, an international standard for biomedical devices.

If desired, the LED emitter system according to the present disclosure can be configured such that it can work in conjunction with infrared spectroscopy. Backscatter from the emitters can be collected to record medical information such as $O_2$ saturation and blood flow.

In particular, according to several embodiments of the present disclosure, an infrared LED array will have one or more following properties: 1) The LED emitter system will use longer wavelengths in the range of 900-1100 nm, which will ensure low absorption and scattering of the energy, resulting in deeper light penetration. 2) The grid will be designed to have one detector and one LED per module. The number of modules in a grid depends on the size of the device. The grid will be designed to uniformly illuminate the brain by use of lenses coupled with LEDs and will be designed to be lightweight and portable. 3) The LED and associated systems will be configured such that the duty cycle and associated circuits (see, e.g., FIGS. 7A, 7B and 8 described above) require ultra-low power and dissipate little to no heat. Estimates predict that the LED array can be driven by two lithium ion batteries with protection circuitry. 4) The LED system operates in a range such that the maximal permissible temperature rise does not exceed 1° C. by using a detector array to adaptively adjust the power of LEDs and thereby controlling the temperature. 5) The array will be addressable and reconfigurable to turn on/off different sections of the grid.

In embodiments herein described, the compound is selected to have chemical and/or biological reactions of interest relative to a biological environment of interest. In particular, chemical or biological reactions characterizing a compound of interest comprise chemical reactions resulting in imaging a targeted biological environment. In some of those embodiments, the caged compound can be a label. In particular, selection of a suitable label can be performed to include label that when caged to the photoacid, are not able to emit the signal and regain the ability emit the signal upon decaging through excitation of the coupled photoacid. Detection of the uncaged label can be performed through suitable detector able to measure the labeling signal emitted by the label at issue that are identifiable by a skilled person.

For example, in embodiment the label is fluorescein, and when caged to the photoacid, the caged fluorescein compound does not fluoresce. Upon decaging through excitation of the light absorbing moiety of the photoacid, fluorescein is expected to be decaged and then exhibit detectable fluorescence through approaches such as fluorescent spectroscopy or microscopy. Additional exemplary labels suitable to be administered as a caged compound herein described are expected to comprise as rhodamine, AlexaFluor dyes, Cy3, and Cy5.

In some embodiments, the compound to be cages is a drug that can be diagnostic or therapeutic, or a candidate drug. In some of these embodiments, the drug is a candidate drug. In an embodiment of a caged candidate drug, the candidate compound can be selected based on one or more of the following properties: 1) having minimal pharmacologic activity in the caged form, 2) following photonic decaging, the decaged form retaining pharmacological activity, 3) being chemically stable in conditions for transport and storage, 4) being be safe and not generate toxic metabolites upon treatment, 5) having acceptable pharmacokinetic and pharmacodynamic profile for entry into the desired site of activity, 6) not requiring special handling, 7) and requiring minimal formulation for administration (see Example 2). Exemplary drugs expected to be deliverable through the methods and systems herein described comprise in some embodiments, the compounds caged by a long wavelength absorber are neurotransmitters, anti-cancer agents, sedatives, antibodies, antibiotics, or protein therapeutics.

In some embodiments, a plurality of caged compounds can be administered simultaneously or sequentially. In this embodiment, separate compounds enter the biological environment, and upon decaging, the compounds are free to chemically or biologically react independently or together. In some embodiments, one compound is an imaging molecule and the separate compound is not an imaging compound. In a further embodiment, positive detection of the imaging compound from decaging indicates decaging of the compound that is not an imaging compound. In other embodiments, the separate compounds released bind together to form a new complex. In other embodiments, one separate molecule enhances the effect of a second separate molecule. In further embodiments, the multiple caged compounds can be caged by different long wavelength absorbers that decage at different wavelengths allowing precise control of decaging.

In embodiments where the uncaged compound can have an established administering protocol possibly associated to specific formulation (e.g. formulation for injection or parenteral administration). In some of those embodiments, administering the caged compound can be performed in accordance with the established protocol possibly following testing to verify specific conditions associated with the caging of the compound at issue. For example, the skilled person can determine administering conditions by testing set doses, formulations, scheduled administration and/or other parameters identifying the administering and by irradiating the biological environment and different intervals for different ranges of time to detect an occurred uncaging. The skilled person can repeat these experiments for every dose investigated. Based on the data, the skilled person determines the timing between administering and irradiating through empirical analysis to determine the optimal length of time between administering the caged compound and the caged compound localizes to the desired site of decaging. These factors are dependent on absorption and diffusion rates of the compound in the specific biological environment and are different for each set of conditions. These factors directly connect to the efficacy and dosage which can be determined by the skilled person through a series of control and variable experiments (see Example 2 and Example 4).

In some embodiments, the administering of caged compounds can be performed to target a "leaky" biological environment that is characterized by an accumulation of fluids (e.g. blood) accompanied by a higher concentration of solutes and target molecules (e.g. cytokines and additional molecule produced in connection with an inflammatory response) (leaky environment). Exemplary leaky environments comprise tissues damaged as a result of an injury. In such embodiments, the site of injury may become "leaky" resulting blood vessel dilation and increased blood flow to the site. Additional exemplary leaky environments can comprise certain tumors and biological environments exhibiting an inflamed response. In those embodiments the administering can be performed taking into account that the difference in concentration, diffusion clearance rate and accumulation of the caged compound in the leaky environment with respect to competing surroundings.

In some embodiments, the administering is performed to target a biological environment exhibiting inflammation or and inflammatory response. The wording "inflammation" and inflammatory response as used herein indicate the complex biological response of vascular tissues of an individual to harmful stimuli, such as pathogens, damaged cells, or irritants, and includes secretion of cytokines and more particularly of pro-inflammatory cytokines, which comprise cytokines which are produced predominantly by activated immune cells such as microglia and are involved in the amplification of inflammatory reactions. Exemplary inflammations include acute inflammation and chronic inflammation. The wording "acute inflammation" as used herein indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). The wording "chronic inflammation" as used herein indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. Chronic inflammation results from several known disease in the art that include asthma, an autoimmune disease, celiac disease, chronic prostatitis, inflammatory disease, pelvic inflammatory disease, arthritis, age related macular degeneration, sarcoidosis, vasculitis, diabetic retinopathy or nephropathy.

In embodiments, wherein the administering is performed to target a biological environment exhibiting inflammation, administered amounts of the caged compound, time of administration and irradiation as well as related wavelengths, can be determined based on the fact that cells exhibiting an inflammatory response can more easily absorb light compared to cells not in an inflammatory state. Exploiting this fact, a skilled person is expected to be able selectively target inflammation sites by exposing the biological environment to irradiation that is above the threshold of power to be absorbed by inflammatory cells, but below the threshold to be absorbed by non-inflammatory cells. The skilled person can determine a suitable range and/or power of irradiation necessary for a desired uncaging for example, through experiments in in vitro, in vivo, and ex vivo samples that are not exhibiting an inflammatory response and separate samples that are exhibiting an inflammatory response as described above by the methods described above.

Figure 2:
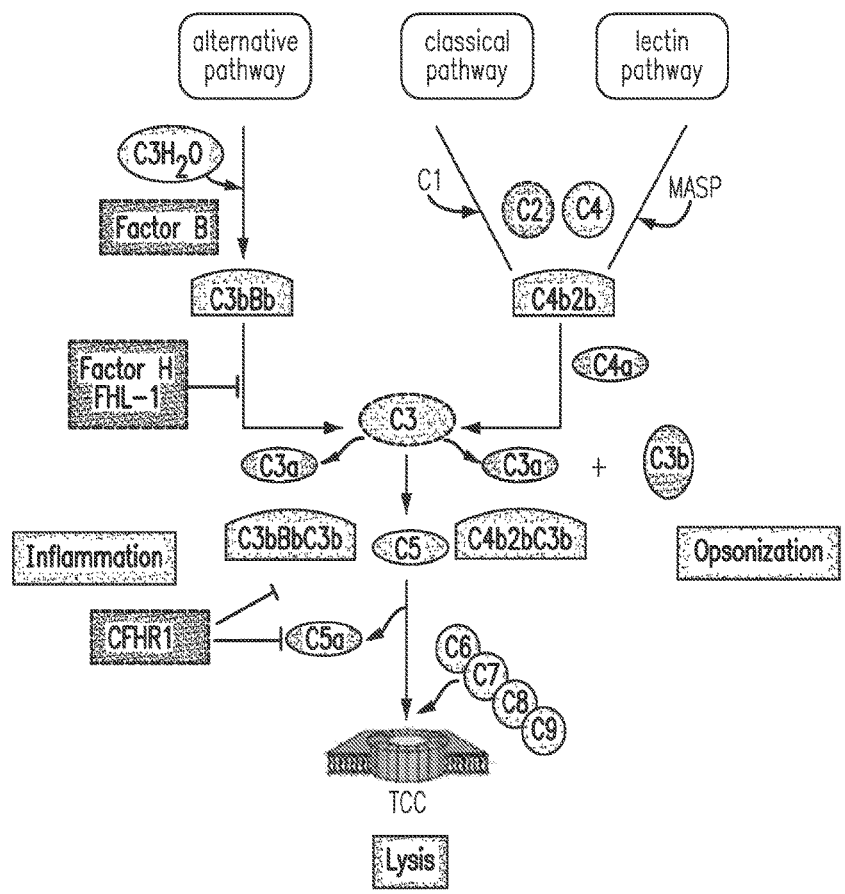
FIG. 2 shows a schematic illustration of three pathways (alternative, lectin, and classical pathway) associated with Age-related Macular Degeneration which can be targeted with a controlled delivery of a caged compound according to embodiments herein described.

In some embodiments, the administering can be performed on an inflamed biologic environment following a traumatic event. In some embodiments the administering can be performed in biologic environment exhibiting a chronic inflammation. An example of chronic inflammation that is associated with lowered pH is age related macular degeneration (AMD, FIG. 2), a condition of the eye. In embodiments wherein the biological environment is the eye, the compound is a neuromodulator. In this embodiment, the neuromodulator is a photoactivated cellular switch injected through intraocular injection. Further in this embodiment, an infrared stimulator in eyeglasses converts visible light to infrared and transmits infrared light into the eye. As a result, cell ion channels impart light sensitivity to these neurons and, by doing so, effectively bypass damaged photoreceptors. This embodiment is a retinal cellular prosthesis that enables light sensing by the retina in the blind. Thus, decaging of the neuromodulator is evident by light sensing.

In some embodiments, the administering can be performed to a target biologic environment presenting an acidic pH (pH less than 7) which can occur in various biologic environments and in particular in a biologic environment presenting an inflammatory response. In particular, in those embodiments the administering can be performed taking into account the effect of the acidic pH on the uncaging of the compound by the photoacid, which is expected to be enhanced. As a result, the administering of a compound caged by a photoacid in a biologic environment having an acidic pH is expected to result in an enhanced deliver of the compound when uncaged by low power infrared light. In some embodiments, compounds also comprise an "armed" synthetic switch. In these embodiments, the "armed" synthetic switch responds to drops in pH of the biological environment.

In some embodiments, a preparation of molecules herein described can be administered to a tissue including neurons to result in a high density neural interface for neuromodulation as well as to be used for localized drug delivery and diagnosis for patients with neurological diseases (e.g., retina, brain, spinal chord, and additional environments identifiable by a skilled person.).

In some embodiments, the biological environment is a brain that has a traumatic injury. In further embodiments, the caged compound is a therapeutic drugs (such as Erythropoietin, Gabapentin (Neurontin®), phenobarbital, N-acetylcysteine, or progesterone) or an imaging molecule (such as fluorescein, rhodamine, Cy2, Cy3, Cy5, Cy7, AlexaFluor molecules). Caged compounds administered to the brain after a traumatic injury can gain access into brain parenchyma through compromised areas of the blood-brain barrier (BBB) during early stages where flow is not severely compromised. When the compound is caged by a photoacid, local pH drops from the traumatic brain injury (TBI) is expected enhance the photoacid effect. In one embodiment, caged drugs can be intravenously injected into the bloodstream of an injured patient. In this embodiment, the caged drug is in circulation and extravasates through the compromised BBB into injured brain tissues and the patient wears a garment that wraps around the skull like a modified balaclava or swimmer cap type hood that is embedded with an array of time-gated infrared (IR) LEDs as depicted FIG. 4B. Optionally, a cervical collar is placed to keep the patient's head secure. In the embodiment, the LEDs embedded in the garment is expected to expose light to trigger the decaging of the drug to treat the injury. This embodiment can be used to treat or triage a patient for subsequent medical procedures.

In accordance with the embodiment shown in FIG. 6, infrared light is applied across the skull to trigger the targeted release of TBI-combating drugs near the area of brain damage. The possibility of drug release in other brain regions is limited by using a synthetic switch that is selectively triggered in the presence of a tissue-specific pH change in the area of early brain injury. FIG. 6 shows a body-worn, infrared-emitting device (600) placed on the injured patient. Device (600) comprises a plurality of modules (610), each module including infrared transmitters and infrared detectors, later shown.

Figure 5A:
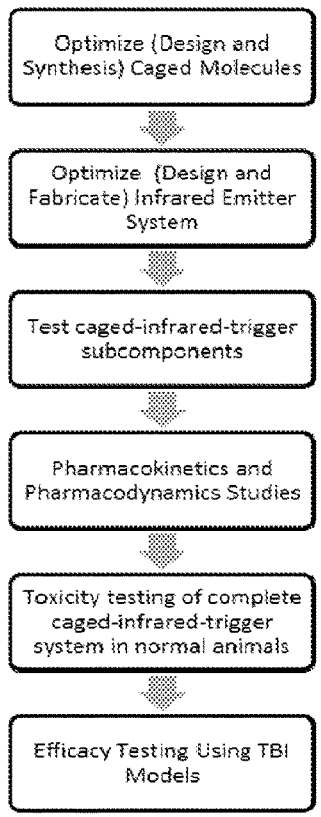
FIG. 5A shows a block diagram related to a method to identify and design a caged compound to be delivered in the brain using traumatic brain injuries (TBI) models according to embodiments of methods and systems herein described.
Figure 5B:
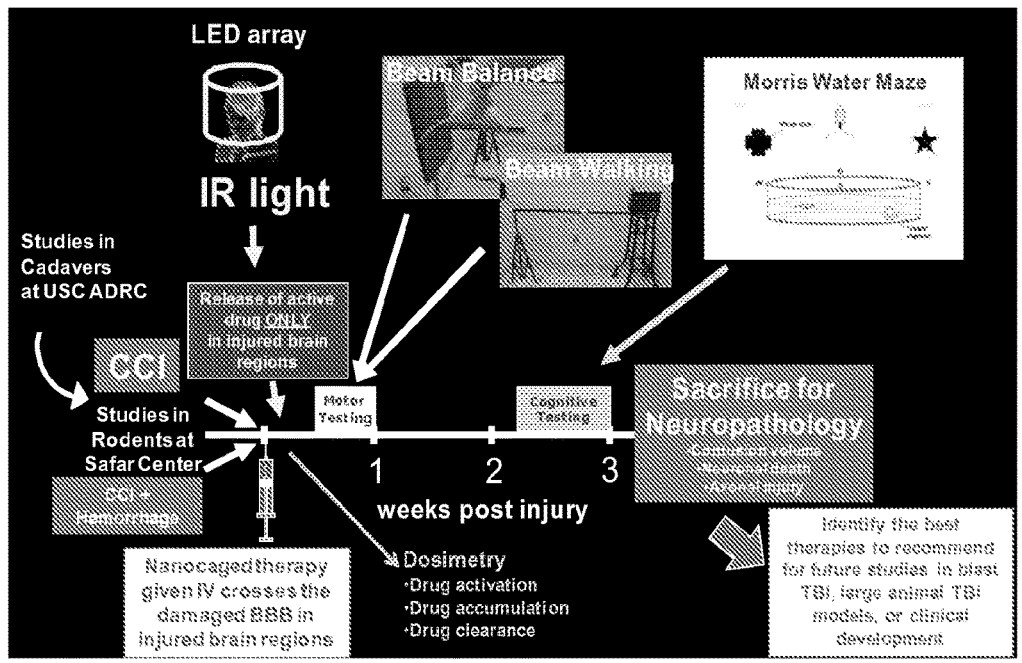
FIG. 5B shows a schematic illustration of a method for therapy development from human cadaveric work to in vivo testing performed using caged compounds herein described, according to embodiments herein described. The illustration of FIG. 5B is provided by the University of Pittsburgh.

A skilled person in the art tests caged compounds for brain injury in a set of experiments as outlined in FIGS. 5A and 5B. In FIG. 5A, both the caged compounds and the infrared emitters can be optimized using benchtop and cellular assays (Activities I and II) as described earlier. Fresh cadaver studies are conducted to help provide a test structure that has similar size and structural and geometrical constraints (Activity III, see Example 3). Upon obtaining an optimized caged compound, pharmacokinetic studies are conducted in vitro (Activity IV, see Example 4). The long wavelength absorber, the caged compound, and the decaged compound after release from light absorption (Activity V) are tested for toxicity in animal models. In addition, the approach is validated in animal models of TBI (VI) as depicted in FIG. 5B.

In some embodiments, a preparation of caged compounds herein described can be used outside the central and peripheral nervous systems to image and treat other body parts including abnormal cellular growth such as that seen in cancer.

In some embodiments, a preparation of caged compounds herein described can be used in laboratory testing of biopsy tissue or parenchymal or hematopoietic cells In some embodiments, the biological environment can be a cell culture. In these embodiments, administering of caged compounds can be performed by providing the caged compound to media of the cell culture. In these embodiments, irradiation is performed by a non-portable or portable device. Distance to the cell culture from the non-portable or portable device is different for each device and power setting and is determined by empirical means as previously described. Decaging is detected by measuring the activity of decaged compound or mass spectroscopic analysis of samples from the cell culture.

In some embodiments, the biological environment is a tumor. In this embodiment, administering of caged compounds comprises direct injection into the tumor. Here, the compound is an anti-cancer drug, a live/dead cell dye, or imaging molecule. In these embodiments, irradiation is performed by a non-portable or portable device. Distance to the tumor from the non-portable or portable device is different for each device and power setting and is determined by empirical means as previously described. Optionally, two caged molecules can be administered where one caged molecule when decaged, visual detection is possible resulting in a positive confirmation that a second caged molecule has been decaged as well. Dosage calculation is done by methods known to a skilled person (see Example 2).

In some embodiments, a preparation of caged compounds herein described which can deliver a payload of drugs, imaging molecules, or modulate neuronal activity, and can be activated upon exposure to light with longer wavelengths (800 nm-1.5 microns), can be administered by injection (e.g. intravenously or directly into tissue such as the vitreous cavity of the eye), ingestion or inhalation, or topically applied to an individual (e.g. as a cream or a drop).

In some embodiments, caged compounds herein described can be provided as a part of systems to administer caged compounds based and decage caged compounds based on irradiation according to methods herein described. In some embodiments, the system can comprise one or more compound of interest caged within a photoacid, and a light emitting device adapted to irradiate light at a wavelength of from about 900 nm to about 1100 nm for simultaneous combined or sequential use in a method of the disclosure.

In some embodiments, the systems herein described can be provided in the form of kits of parts. In a kit of parts, a long wavelength absorber, a compound, reagents necessary to cage the compound in the long wavelength absorber, devices suitable to administer the caged the compound to a biological environment, and a light source to emit a wavelength in a range from 900-1100 nm. In some embodiments, the systems to systems to perform administering and the decaging of caged compounds herein described can be provided in the form of kits of parts. In a kit of parts, one or more long wavelength absorbers, compounds, and other reagents to perform the reactions can be comprised in the kit independently. The long wavelength absorber or compound can be included in one or more compositions, and each compound can be in a composition together with a suitable vehicle.

In particular, in some embodiments, the caged compound herein described can be comprised in a composition together with a suitable vehicle. The term "vehicle" as used herein indicates any of various media acting usually as solvents, carriers, binders or diluents for the caged compounds that are comprised in the composition as an active ingredient.

In particular, the composition including the caged compound can be used in one of the methods or systems herein described. In some embodiments, the composition is a pharmaceutical composition and the vehicle is a pharmaceutically acceptable vehicle. In those embodiments one or more caged compounds herein described can be included in pharmaceutical compositions together with an excipient or diluent. In particular, in some embodiments, disclosed are pharmaceutical compositions which contain at least one caged compound as herein described, in combination with one or more compatible and pharmaceutically acceptable vehicles, and in particular with pharmaceutically acceptable diluents or excipients. In those pharmaceutical compositions the caged compound can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "excipient" as used herein indicates an inactive substance used as a carrier for the active ingredients of a medication. Suitable excipients for the pharmaceutical compositions herein described include any substance that enhances the ability of the body of an individual to absorb the multi-ligand capture agents or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

Further characteristics of the present disclosure will become more apparent hereinafter from the following detailed disclosure by way or illustration only with reference to an experimental section.

EXAMPLES

The caged compounds, compositions methods and system herein described are further illustrated in the following examples, which are provided by way of illustration and are not intended to be limiting.

In particular, the following examples illustrate exemplary caged compound delivery methods and systems and related compounds and compositions. A person skilled in the art will appreciate the applicability and the necessary modifications to adapt the features described in detail in the present section, to additional caged compounds, methods and systems according to embodiments of the present disclosure.

Example 1

Photoacids as Long Wavelength Absorbers

Exemplary photoacids caging a compound of interest comprise photoacids of Formula (I) wherein $R^4$ is

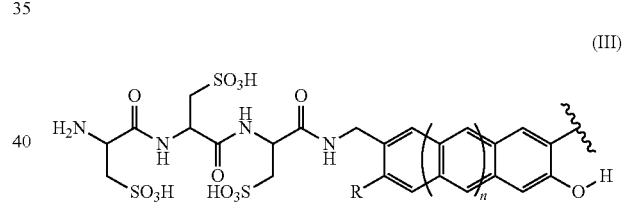

(III)

wherein R is $CH_2NH_2$ or another polysulfonate peptide moiety, and n is between 0 and 5; or a compound according to Formula (IV):

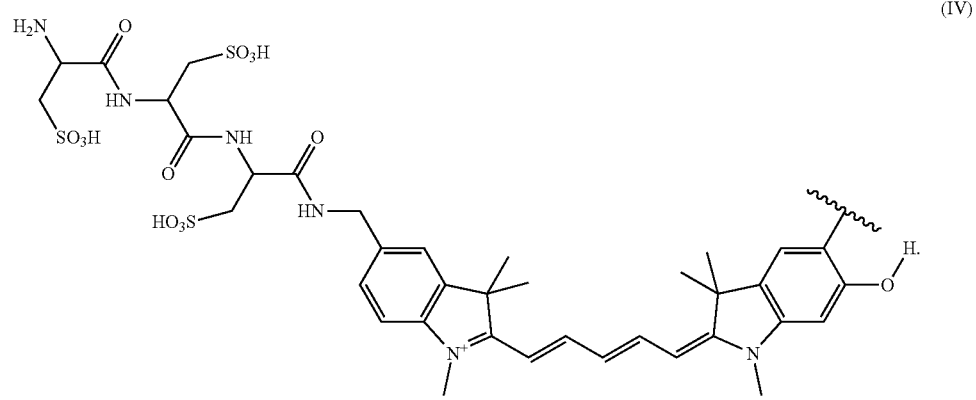

(IV)

FIG. 1 exemplifies uncaging of a compound caged with a long wavelength absorber. The compound is labeled as a drug that is linked to a NIR absorber. Upon NIR irradiation, the linker is cleaved allowing release or decaging of the drug.

In particular, a photoacid compound is expected to be decaged in vitro using the following procedure. In a quartz cuvette, the photoacid compound (0.001 M) is dissolved in spectroscopic-grade acetonitrile and irradiated at 300 nm using a 1-kW xenon arc lamp at room temperature for 15 minutes. Aliquots are removed and analyzed by analytical LC-MS utilizing a gradient elution of 10-100% acetonitrile-water over 10 minutes. The data shown represents t=0 minutes in the lower LC-MS trace, t=15 minutes in the upper LC-MS trace.

Suitable adjustments for decaging in vivo and/or with specific compound are identifiable by a skilled person upon reading of the present disclosure.

Example 2

Identification of Lead Candidate Etomidate- and Cyclosporine-Based Caged Compounds Techniques used to identify lead candidate caged and photonically decaged etomidate- and cyclosporine-based nanocaged compounds are described herein. The biological activity of caged and decaged etomidate- and cyclosporine-based nanocaged compounds is expected to be suitable in established ion channel and interleukin-2 (IL-2) inhibition assays, respectively. Candidates with a 50% effective concentration (EC50) with near equivalent with the decaged compound following photonic liberation can be further evaluated. The effect of ambient pH on decaging can also be determined, since necrotic tissue are more acidic as compared to normal tissue. The pH of the medium is expected to be adjustable using lactic acid, so that the final pH will be 7.4, 6.0 and 5.0. The level and rate of decaging will be determined before and after photonic decaging over time, where the active moiety and its metabolites will be measured using LC-MS assay.

Determining the Level of Decaging: the level and time required to liberate the active moiety can be determined using a time course study. The time of IR activation can be initially performed in biological assays performed in in vitro. Caged compounds can be incubated in medium and undergo photonic decaging. The time require to and extend of active drug liberation can be determined using ion channel and IL-2 inhibition assay to evaluate etomidate- and cyclosporine-caged compounds, respectively. The intensity of infrared excitation can be varied to determine the optimal wavelength and timing required to maximally liberate the active moiety. In addition, the impact of microenvironment pH on decaging of the active moiety can be determined by adjusting the medium pH at 7.4, 6.0 and 5.0. To affirm that biological activity is a direct consequence of decaging the active moiety, medium is collected to determine the levels of caged and decaged compounds via LC-MS. An increasing ratio of decaged versus nanocaged is expected to guide in the identification of the hit compounds.

Ion Channel Inhibition Assay: HEK293 cells with heterologous expression of α4 and β3 subunits of GABA(A) receptor, using transfection with DEAE-dextran, are used in inhibition assays. Whole-cell currents can be recorded at a holding potential of −60 mV (EPC-9 amplifier, HEKA Elektronik, controlled by Pulse software) elicited by drug candidates at a range of concentrations, that has or has not undergone photonic decaging, and applied via a home-built, multibarrel, gravity-fed, solenoid-gated application system, that has an exchange time of ~10 ms. The external solution can contain (in mM): 142 NaCl, 1 CaCl2, 6 MgCl2, 8 KCl, 10 glucose, and 10 HEPES, pH 7.4 (~300 mOsm). The pipette internal solution can contain in mM: 140 CsCl, 4 NaCl, 0.5 CaCl2, 10 HEPES, 5 EGTA, 2 Mg2+, ATP, and 0.2 GTP. Pipettes can be pulled using a standard Narishige puller. Pipette resistance can be ~4 MOhms.

CSA Biological Activity: Human mammary epithelial cells (HMEC) can be incubated for 2 hours with cyclosporine (CSA) or the caged-CSA that has or has not undergone photonic decaging. IL-2 biological activity can be determined using NO elaboration and eNOS expression. Medium can be collected and the level of NO can be determined using Griess reaction. In addition the cells can be collected and total RNA can be isolated using TRIzol reagent (Invitrogen) to determine the level of eNOS expression.

Metabolic Fate Analysis: Lead candidate(s) can be assessed for metabolic fate using hepatic microsomes derived from male Sprague-Dawley (In Vitro Technologies, Baltimore, Md.). Five μL 100 μM lead compound can be added into glass vials and heated at 37° C., where 395 μL microsomes (20 mg/mL) suspended in 0.1 M PBS (pH 7.4) can be added and incubated for 3 min. The reaction is initiated by adding 100 μL 50 mM NADPH in 0.1 M PBS, pH 7.4. At 8 time points, from 3 to 90 min, 50 μL can be removed, and reaction quenched using 300 μL MeOH that contains an appropriate IS control. Samples can then be centrifuged at 300×g for 20 min at 4° C., where the supernatant can be scanned for metabolites using LCQ Deca LC-MS. The structure of the metabolites can be reconstructed using deconvolution of the parent compound. The kinetics of metabolite formation and clearance can be analyzed using a linear fit of the natural logarithm of the ratio of the compound peak area to the internal standard peak area against time. A control reaction (without NADPH co-factor) can be used in order to assess the amount of thermal breakdown, insolubility and non-specific binding that contributes to the overall loss of the test compound. Using the assumption that the substrate concentration of 1 μM, Km, CLint values can be calculated from the negative slope of the linear fit divided by the microsomal concentration.

Pharmacokinetics and Toxicokinetics Study in Mice: Lead candidate can be assessed for pharmacokinetic and toxicokinetics. C57BL can be administered a dosage and randomly assigned to 1 of 7 time points for blood collection. At time of sacrifice, blood and vital organs can be harvested for histological evaluation for organ toxicity. Blood concentrations of the lead candidates can be collected after an IV dose, 100 μL blood can be taken from the saphenous vein of two mice per time point at end of dosage; 0, 0.5, 1, 2, 4, 8, and 24 after the end of IV dosage. The drug levels can be measured in the plasma and the specified organs as aforementioned above using LC-MS. Organs can be histologically graded for toxicity.

LC-MS Assays: A validated LC-MS assay is used to determine the intact caged compound, free decaged active moiety, and the uncoupled caged carrier molecule. Multiple reaction monitoring (MRM) signatures can be specifically determined for the cage and decaged compounds, permitting the development of multiplex assay where all of the analytes can be determined simultaneously. The assays are validated for culture medium and plasma samples. Samples are extracted using a using liquid-liquid extraction to remove protein, where the insoluble proteins can be separated by centrifugation. The supernatant can be evaporated to dryness, and reconstituted with 50 μL of running buffer. Separation of the analytes can be performed using C18 reverse phase columns, and the analytes can be quantified using the specific MRMs for each of the analytes.

Example 3

Figure 3:
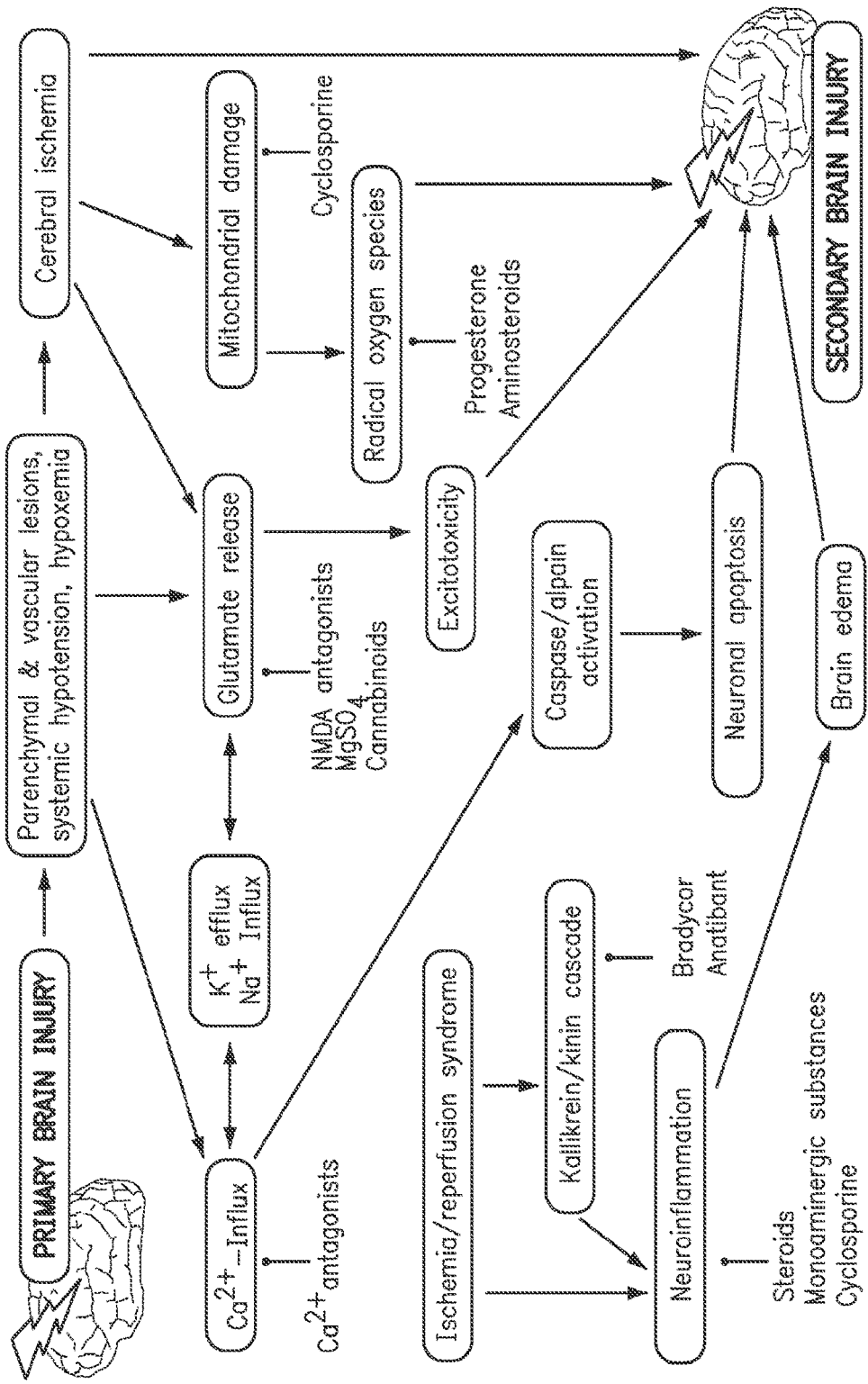
FIG. 3 shows a schematic illustration of a cascade of events upon primary brain injury which can be targeted with a controlled delivery of a caged compound according to embodiments herein described.
Figure 4A:
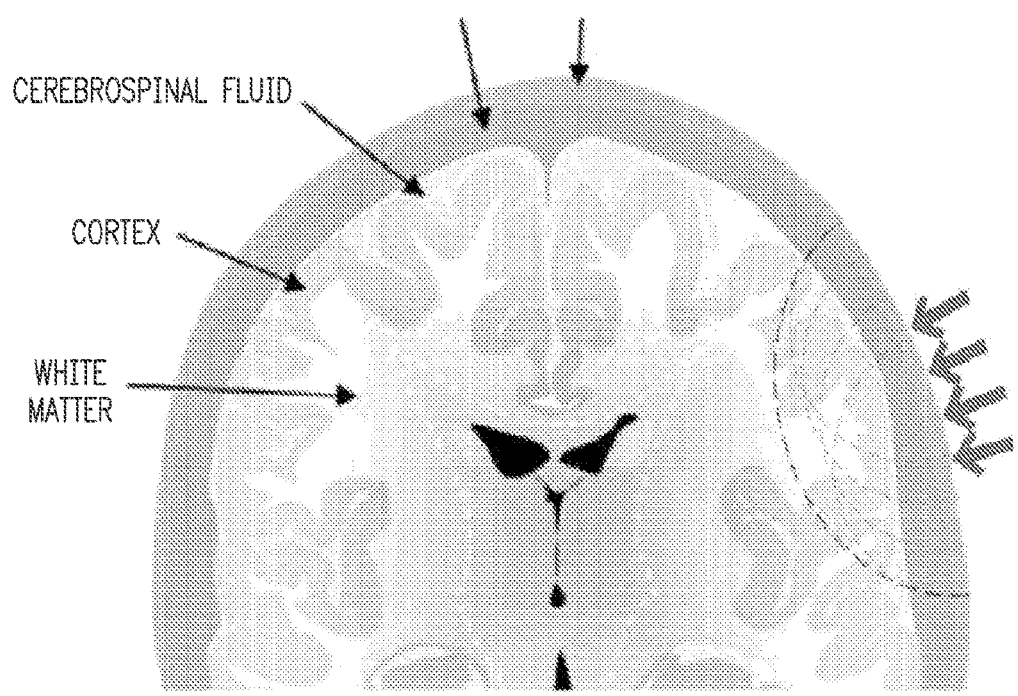
FIG. 4 show a schematic illustration of a diagram of penetration of infrared wavelength into brain tissue (FIG. 4A) a CT scan of a patient with traumatic brain injury (FIG. 4B) as well as a design to intravenous administer a caged-drug complex that is photonically decaged in areas of brain injury by a wearable time-gated LED emitter array contoured to fit the skull (FIG. 4C).

Human Cadaver Tests to Demonstrate Feasibility of Local Release of Fluorescent Marker and Drug Human cadavers are the biological environment used to identify the release of caged fluorescent and drug compounds. In this particular example, human heads cadavers are used. The results of these experiments are analogous to live patient treatment from traumatic brain energy. FIG. 3 depicts a cascade of events upon primary injury, which includes neuroinflammation. Long wavelength visible and NIR radiation can penetrate deeper into tissue than light of shorter wavelength, and by treating at the site of neuroinflammation, secondary brain injury is diminished. FIG. 4A shows that the penetration is significant (left) and highly impactful in the case of TBI (right). In particular, near-infrared radiation NIR at 50 $\mu W/cm^2$ penetrates 8 cm into the brain. Sunlight has 10 $mW/cm^2$ in the NIR range. The quantum energy available at this wavelength within a safe thermal budget is nominal.

Figure 4B:
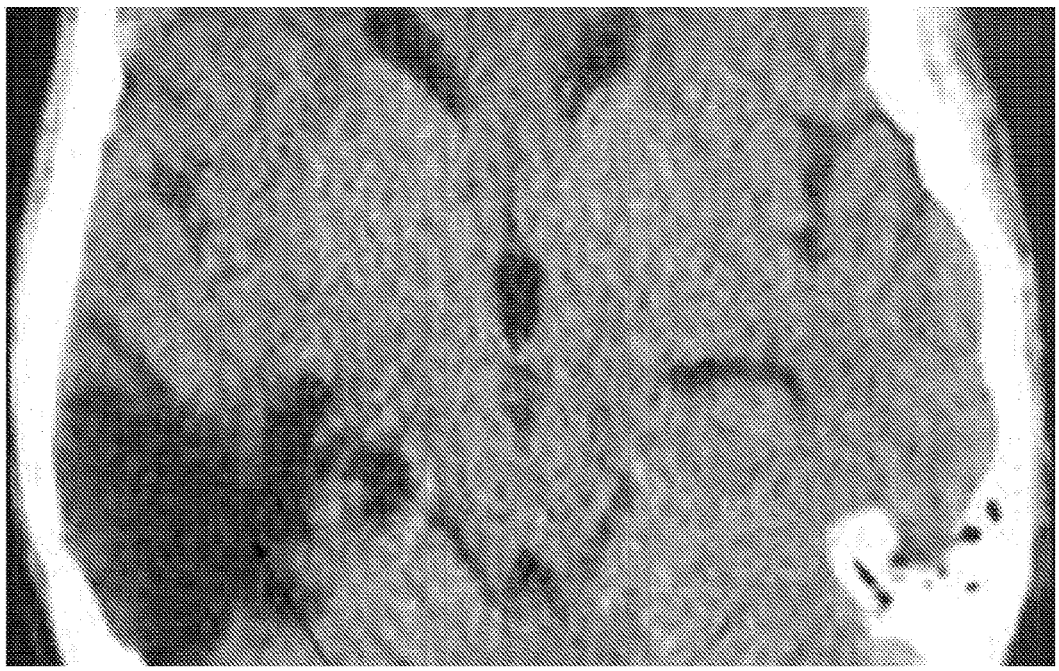
Figure 4C:
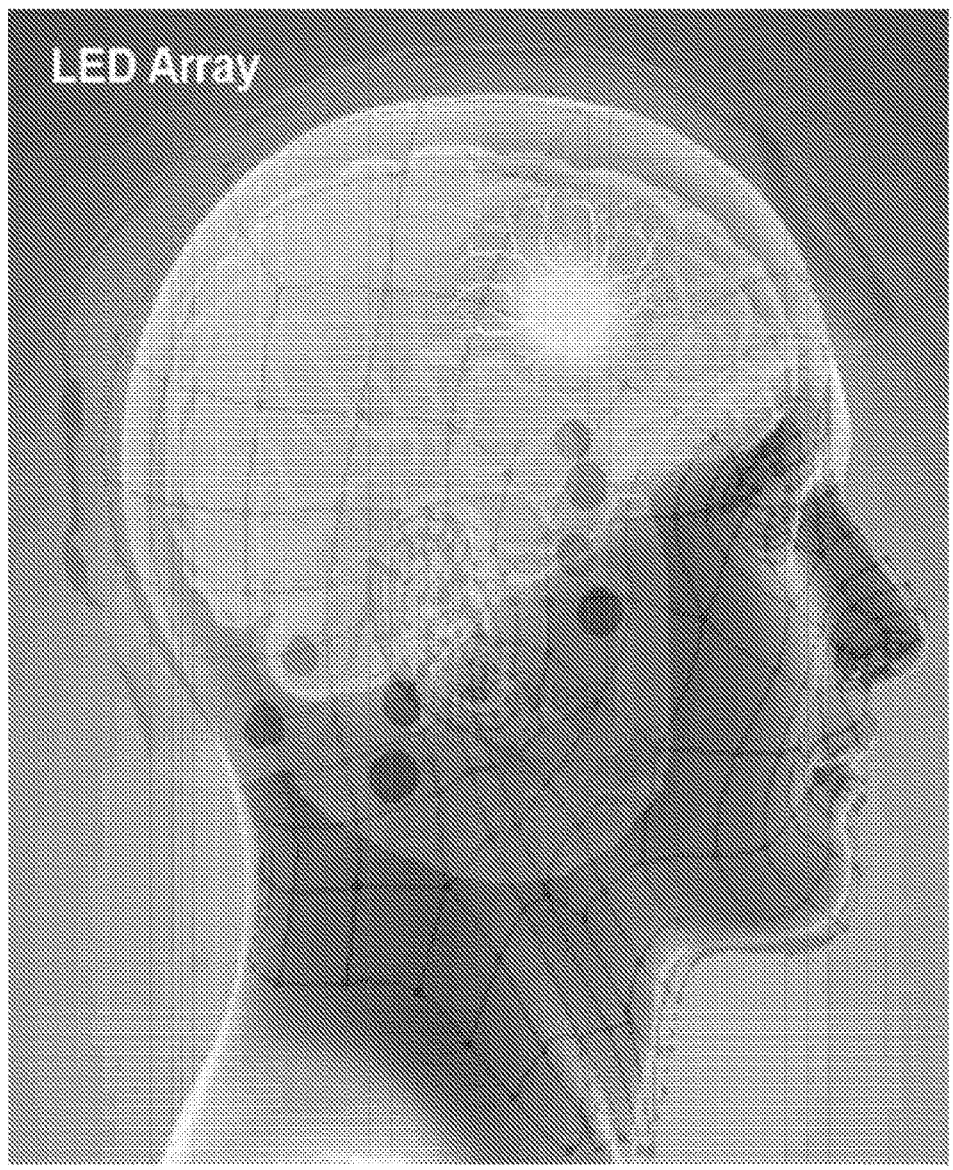

NIR emitters and detectors are placed non-invasively across the human skull to detect the transmission of the selected wavelengths and adjust the energy of the LED emitters appropriately as depicted in FIG. 4B. Transmission can be tested across at least 16 separate points using either moveable single LED transmitters or a grid of programmable and reconfigurable 16 LED transmitters (LED portals can be placed in a "balaclava" like head piece). This is expected to provide a map over the thinner temporal and thicker occipital and frontal parts of the skull. In another test, standard neurosurgical procedures are used to implant deep brain stimulating electrodes to introduce a custom optical-fluidic probes. After a straight-line coronal incision is created at Kocher's point measuring approximately 2 cm anterior to the coronal suture and at the midpupillary line a single burr hole can be created. The aperture can then be augmented using a saw blade to create a craniotomy approximately 3 cm in diameter. The dura can be fenestrated in a cruxiate fashion and the blunt-tipped cannulated introducer can be advanced certain fixed distances as confirmed by centimeter markings on the periphery of the cannula and both distance and general location confirmed by intraoperative ultrasound guidance. The stylette can be removed from the cannula and the optical-fluidic brain probe introduced. The probe can be placed at varying depths and allow us to generate a penetration-depth map for the extracranial LED source (see details under methodology of LED systems). Both cadaver tests are performed with caged compounds of choice, but in particular caged-fluorescein and caged-drug (etomidate and cyclosporine) are described here. After a craniotomy made in the fashion described above, cryoprobe can be applied to the brain tissue to create a localized area of blood-brain damage.

To evaluate the level of diffusion and accumulation in the brain tissues, both caged or decaged compounds can be given as a parenteral infusion into warmed heparinized blood at a rate of 75 cc/hr. The level of accumulation and decaging can be determined using two methods, 1) photonic decaging of fluorescein from the cage compound and 2) quantification of caged drugs and photonically decaged compounds.

Specifically, the caged-compounds (e.g. fluorescein or drug coupling) can be injected in warmed heparinized blood (98.6° F.) via the carotids (infusion can be maintained at 75 cc/hour). The infused cage-compound system is then activated at site of injury using an extracranial LED system. The following treatment groups and controls can be employed; 1) cryotherapy with NIR illumination (treatment group) and the three controls 2) cryotherapy without NIR illumination, 2) no cryotherapy and IR illumination, and 3) no cryotherapy and no NIR illumination. All four of these can be conducted in same cadaver head so as to reduce the number of cadavers needed.

The level of fluorescein liberated is determined by measuring the amount of fluorescence found in the tissue. Fluorescent images (with zooming features turned off) can be taken under a fluorescent lamp. The level of fluorescence can be quantified in the images using ImageJ software using both intensity and area of fluorescence detection. To confirm the level of fluorescence, the fluorescein marker can be collected from injured brain tissue, and extracted using methanol. Following centrifugation, the level of fluorescence in the supernatant can be measured. The various treatments can be compared to determine the level of decaging.

In the caged drug studies, the concentration can be determined using a multiplex LCMS. The level of liberated active drug is expected to quantify the amount of nanocage and decaged compounds simultaneously. To determine whether the impact of therapy through data collected for cadaver experiments, cadavers can be histologically evaluated and compared: 1) normal brain, 2) cryotherapy+illuminated, 3) cryotherapy−illuminated, and 4) normal area+illumination.

Example 4

Efficacy and Dosage Optimization Study Using TBI Animal Models

In this example, two animals models are described (CCI in rats and CCI plus hemorrhage in mice) to determine the efficacy and dosage of caged compounds for traumatic brain injury. Dosimetry can be determined for the rodent models to achieve similar activation parameters at the level of injury in pilot studies. The drug and NIR dosimetry can then be optimized, again in pilot studies in mice. For the in vivo work, the CCI mouse model can be used and the groups for testing can include 1) sham, 2) TBI plus vehicle, 3) TBI plus drug, 4) TBI plus drug plus IR light, and 5) TBI plus IR light alone. Rats and mice can be followed over a one-month period after TBI undergo both comprehensive motor and cognitive outcome evaluations along with neuropathology. The primary outcome parameter can be cognitive outcome (latency to find the hidden platform in the Morris water maze paradigm). Selected drugs can be tested in the rat CCI model. An overview is shown in the FIG. 5B. For each study, the groups for testing can include all of the appropriate controls, namely, 1) sham, 2) TBI plus vehicle, 3) TBI plus drug, 4) TBI plus drug plus IR light, and 5) TBI plus IR light alone. In the long-term outcome studies, rats and mice can be followed for 1-mo after TBI and can undergo comprehensive motor and cognitive testing along with neuropathology. The primary outcome parameter is expected to be cognitive outcome (latency to find the hidden platform in the Morris water maze paradigm).

Beam Balance: Vestibulomotor function can be assessed in mice using a beam-balance task, wire grip, and a Morris water maze (MWM: The mouse MWM consists of a white pool (83 cm diameter, 60 cm deep) filled with water to 29 cm and goal platform (clear plastic, 10 cm diameter) is positioned 1 cm below the water's surface ~15 cm from the southwest wall. The rat MWM employs a 180 cm in diameter and 60 cm high pool filled with water (28 cm depth). A platform 10 cm in diameter and 26 cm high (2 cm below the water's surface) can be used as the hidden goal. A video camera above the pool records swim movement (PC-based tracking). Motor performance during cognitive tests can also be assessed by measuring swim speed in MWM testing to ensure that cognitive performance is not confounded by motor deficits.

Spatial Learning Test: The hidden platform task assesses ability to learn spatial relations between cues and the escape platform (4 daily trials over 7 d). The last 2 d consist of a visible platform task—to control for non-specific visual or motor deficits. A probe trial is also measured. All testing can be conducted under blinded conditions. Data analysis for functional testing is expected to be carried out using two-way ANOVA for repeated measures.

Neuropathology (CCI and CCI+HS): At the designated time, mice can be anesthetized with isoflurane and perfused (10% buffered formalin). The brain can be post-fixed and cryoprotected. Coronal sections can be cut (1.0 mm). Brain sections can be stained with H&E. The lesion areas and non-injured hemispheres are determined in each section by a blinded observer by image analysis. Lesion and hemispheric volumes are calculated. Contusion volume is assessed and expressed in mm3 in the injured hemisphere, and as a % of non-injured hemisphere. Cells in CA1 and CA3 regions is expected to be quantified by stereology in an unbiased manner (StereoInvestigator software 7.50.1, MicroBrightField).

Example 5

Exemplary Prototype to Product Design of a Wearable Array Around a Skull

A method to fabricate the above described wearable array can be divided into three steps:

Step 1: Initial prototype: the layout of the grid and properties of the optical devices (LEDs, lenses and detectors) are determined using 3D electromagnetic (EM) simulations and results from the testing procedure described in Example 3. The constraints are expected to be the maximum and minimum optical intensity to achieve close-to-uniform and safe illumination. The electronics and integrated circuits are expected be specified for a low-power addressable array. As a first solution the array can be divided into a number of sub-arrays. These small sub-arrays can have flat surfaces, but are expected to be connected over a flexible membrane to create a curved shape approximating the curvature of human and/or animal head.

Step 2: Revised prototype aiming to: a) insure reliability, b) reduce power and weight, c) optimize the devices based on measurements of initial prototype.

Step 3: Final product design: based on steps 1 and 2, design an ergonomic, curve fitting, wearable system using technologies such as fabric of optical fibers, integrated with photonic and electronic devices. This step can be performed according to some embodiments, to also use input from the end users in the field in order to make it portable and rugged.

As mentioned in step 1 above, EM simulations can be used to determine the layout of the grid and properties of optical devices. FIG. 10 and FIG. 11 show preliminary results from 2D EM simulations. As mentioned above, the parameters that can be changed and/or optimized are: number of LEDs, power per LED, the distance of the array from the skull, separation between LEDs and LED/lens viewing half angle. There are trade-offs between these parameters and level of uniformity (inside the brain), power consumption and weight of the system. As shown in FIG. 11, in the absence of a lensing system, the array should be placed about 3 cm far from the skull to achieve good uniformity inside the brain. This distance can be used if a lensing system is added to the design.

In summary, in embodiments described herein compounds are described that are capable of being "caged", chemically and/or physically connected to a long wavelength absorber, a moiety capable of absorbing a wavelength greater than or equal to 750 nm. Caged compounds are then capable of being decaged, where the decaged molecules are capable of participating in biological and/or chemical reaction independent of the long wavelength absorber. Decaging is accomplished by excitation of the long wavelength absorber The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "hydrocarbyl" as used herein refers to any univalent radical, derived from a hydrocarbon, such as, for example, methyl or phenyl. The term "hydrocarbylene" refers to divalent groups formed by removing two hydrogen atoms from a hydrocarbon, the free valencies of which may or may not be engaged in a double bond, typically but not necessarily containing 1 to 20 carbon atoms, in particular 1 to 12 carbon atoms and more particularly 1 to 6 carbon atoms which includes but is not limited to linear cyclic, branched, saturated and unsaturated species, such as alkylene, alkenylene alkynylene and divalent aryl groups, e.g., 1,3-phenylene, —$CH_2CH_2CH_2$-propane-1,3-diyl, —$CH_2$-methylene, —CH═CH—CH═CH—. The term "hydrocarbyl" as used herein refers to univalent groups formed by removing a hydrogen atom from a hydrocarbon, typically but not necessarily containing 1 to 20 carbon atoms, in particular 1 to 12 carbon atoms and more particularly 1 to 6 carbon atoms, including but not limited to linear cyclic, branched, saturated and unsaturated species, such as univalent alkyl, alkenyl, alkynyl and aryl groups e.g. ethyl and phenyl groups.

The term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, and additional groups identifiable by a skilled person, and examples of heteroatom-containing alicyclic groups are pyrrolidino, morpholino, piperazino, piperidino, and additional substituents identifiable by a skilled person.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "alkylamino" as used herein intends an alkyl group bound through a single terminal amine linkage; that is, an "alkylamino" may be represented as —NH-alkyl where alkyl is as defined above. A "lower alkylamino" intends a alkylamino group containing 1 to 6 carbon atoms. The term "dialkylamino" as used herein intends two identical or different bound through a common amine linkage; that is, a "dialkylamino" may be represented as —N(alkyl)$_2$ where alkyl is as defined above. A "lower dialkylamino" intends a alkylamino wherein each alkyl group contains 1 to 6 carbon atoms. Analogously, "alkenylamino", "lower alkenylamino", "alkynylamino", and "lower alkynylamino" respectively refer to an alkenyl, lower alkenyl, alkynyl and lower alkynyl bound through a single terminal amine linkage; and "dialkenylamino", "lower dialkenylamino", "dialkynylamino", "lower dialkynylamino" respectively refer to two identical alkenyl, lower alkenyl, alkynyl and lower alkynyl bound through a common amine linkage. Similarly, "alkenylalkynylamino", "alkenylalkylamino", and "alkynylalkylamino" respectively refer to alkenyl and alkynyl, alkenyl and alkyl, and alkynyl and alkyl groups bound through a common amine linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "arene", as used herein, refers to an aromatic ring or multiple aromatic rings that are fused together. Exemplary arenes include, for example, benzene, naphthalene, anthracene, and the like. The term "heteroarene", as used herein, refers to an arene in which one or more of the carbon atoms has been replaced by a heteroatom (e.g. O, N, or S). Exemplary heteroarenes include, for example, indole, benzimidazole, thiophene, benzthiazole, and the like. The terms "substituted arene" and "substituted heteroarene", as used herein, refer to arene and heteroarene molecules in which one or more of the carbons and/or heteroatoms are substituted with substituent groups.

The terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo", "halogen", and "halide" are used in the conventional sense to refer to a chloro, bromo, fluoro or iodo substituent or ligand.

The term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO$^-$), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-(C5-C24 aryl)-substituted carbamoyl (—(CO)—NH-aryl), di-(C5-C24 aryl)-substituted carbamoyl (—(CO)—N(C5-C24 aryl)2), di-N—(C1-C24 alkyl), N—(C5-C24 aryl)-substituted carbamoyl, thiocarbamoyl (—(CS)—NH2), mono-(C$_1$-C24 alkyl)-substituted thiocarbamoyl (—(CO)—NH (C1-C24 alkyl)), di-(C1-C24 alkyl)-substituted thiocarbamoyl (—(CO)—N(C1-C24 alkyl)2), mono-(C5-C24 aryl)-substituted thiocarbamoyl (—(CO)—NH-aryl), di-(C5-C24 aryl)-substituted thiocarbamoyl (—(CO)—N (C5-C24 aryl)2), di-N—(C1-C24 alkyl), N—(C5-C24 aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, and additional imino identifiable by a skilled person.), C2-C20 alkylimino (CR=N(alkyl), where R=hydrogen, C1-C24 alkyl, C5-C24 aryl, C6-C24 alkaryl, C6-C24 aralkyl, and additional alkylimino identifiable by a skilled person.), arylimino (—CR=N(aryl), where R=hydrogen, C1-C20 alkyl, C5-C24 aryl, C6-C24 alkaryl, C6-C24 aralkyl, and additional arylimino identifiable by a skilled person.), nitro (—NO2), nitroso (—NO), sulfo (—SO2-OH), sulfonato (—SO2-O$^-$), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), (C5-C24 arylsultinyl (—(SO)-aryl), C1-C24 alkylsulfonyl (—SO2-alkyl), C5-C24 arylsulfonyl (—SO2-aryl), boryl (—BH2), borono (—B(OH)2), boronato (—B (OR)2 where R is alkyl or other hydrocarbyl), phosphono (—P(O)(OH)2), phosphonato (—P(O)(O$^-$)2), phosphinato (—P(O)(O$^-$)), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Corrigan J D, Selassie A W, Orman J A. The epidemiology of traumatic brain injury. J Head Trauma Rehabil. 2010; 25(2):72-80.
2. Sauaia A, Moore F A, Moore E E, Moser K S, Brennan R, Read R A, Pons P T. Epidemiology of trauma deaths: a reassessment. J Trauma. 1995; 38(2):185-93.
3. Narayan R K, Michel M E, Ansell B, et al. Clinical trials in head injury. J Neurotrauma. 2002; 19(5):503-57.
4. Granacher R P, Traumatic Brain Injury: Methods for Clinical & Forensic Neuropsychiatric Assessment, 2nd Ed. Boca Raton: CRC. pp. 26-32. ISBN 0-8493-8138-X
5. Giza C C, Hovda D A. The neurometabolic cascade of concussion. J of Athletic Training 2001; 36(3):228-235
6. Martland H S. Punch Drunk, JAMA 1928; 91:1103-7
7. Plassman B L, Havlik R J; Steffens D C, et al. Documented head injury in early adulthood and risk of Alzheimer's disease and other dementias. Neurology 2000; 55(8):1158-1166
8. Lye T C and Shores E A. Traumatic brain injury as a risk factor for Alzheimer's disease: A review. Neuropsych Rev 2000; 10:115-129
9. Garga N, Lowenstein D H. Posttraumatic epilepsy: a major problem in desperate need of major advances. Epilepsy Curr. 2006; 6(1):1-5.
10. Bower J H, Maraganore D M, Peterson B J, et al. Head trauma preceding PD: a case-control study. Neurology. 2003; 60(10):1610-5.
11. Kochanek P M, Carney N, Adelson P D, et al. Guidelines for the acute medical management of severe traumatic brain injury in infants, children, and adolescents—second edition. Pediatr Crit Care Med. 2012; 13 Suppl 1:S1-82.
12. Cohn B F, Rejger V, Hagenouw-Taal J C, Voormolen J H. Results of a feasibility trial to achieve total immobilization of patients in a neurosurgical intensive care unit with etomidate. Anaesthesia. 1983; 38 Suppl:47-50.
13. Bergen J M, Smith D C. A review of etomidate for rapid sequence intubation in the emergency department. J Emerg Med 15:221-30, 1997.
14. Adnet F, Minadeo J P, Finot M A, Borron S W, Fauconnier V, Lapandry C, Baud F J. A survey of sedation protocols used for emergency endotracheal intubation in poisoned patients in the French prehospital medical system. Eur J Emerg Med 5:415-9, 1988
15. Murugaiah K D, Hemmings H C Jr. Effects of intravenous general anesthetics on [3H]GABA release from rat cortical synaptosomes. Anesthesiology 89:919-28, 1998
16. Watson J C, Drummond J C, Patel P M, Sano T, Akrawi W, U H S. An assessment of the cerebral protective effects of etomidate in a model of incomplete forebrain ischemia in the rat. Neurosurgery 30:540-4, 1992
17. Patel P M, Goskowicz R L, Drummond J C, Cole D J. Etomidate reduces ischemia-induced glutamate release in the hippocampus in rats subjected to incomplete forebrain ischemia. Anesth Analg 80:933-9, 1995
18. Albensi B C, Sullivan P G, Thompson M B, Scheff S W, Mattson M P: Cyclosporin ameliorates traumatic brain-injury induced alterations of hippocampal synaptic plasticity. Exp Neurol 162:385-389, 2000
19. Hatton J et al. Dosing and safety of cyclosporin in patients with severe brain injury J Neurosurgery 2008; 109: 699-707.
20. G. Grasso, "Neuroprotective effect of recombinant human erythropoietin in experimental subarachnoid hemorrhage," Journal of Neurosurgical Sciences, vol. 45, no. 1, pp. 7-14, 2001.
21. E. Morishita, S. Masuda, M. Nagao, Y. Yasuda, and R. Sasaki, "Erythropoetin receptor is expressed in rat hippocampal and cerebral cortical neurons, and erythropoietin prevents in vitro glutamate-induced neuronal death," Neuroscience, vol. 76, no. 1, pp. 105-116, 1996.
22. M. Bernaudin, H. H. Marti, S. Roussel, et al., "A potential role for erythropoietin in focal permanent cerebral ischemia in mice," Journal of Cerebral Blood Flow and Metabolism, vol. 19, no. 6, pp. 643-651, 1999.
23. C. Alafaci, F. Salpietro, G. Grasso, et al., "Effect of recombinant human erythropoietin on cerebral ischemia following experimental subarachnoid hemorrhage," European Journal of Pharmacology, vol. 406, no. 2, pp. 219-225, 2000.
24. H. H. Marti, M. Gassmann, R. H. Wenger, et al., "Detection of erythropoietin in human liquor: intrinsic erythropoietin production in the brain," Kidney International, vol. 51, no. 2, pp. 416-418, 1997.
25. S. E. Juul, S. A. Stallings, and R. D. Christensen, "Erythropoietin in the cerebrospinal fluid of neonates who sustained CNS injury," Pediatric Research, vol. 46, no. 5, pp. 543-547, 1999.
26. DeWitt D S, Prough D S. Blast-induced brain injury and posttraumatic hypotension and hypoxemia. Neurotrauma 26:877-87, 2009.
27. Hovda D A, Lee S M, Smith M L, Von Stuck S, Bergsneider M, Kelly D, Shalmon E, Martin N, Caron M, Mazziotta J, et al. The neurochemical and metabolic cascade following brain injury: moving from animal models to man. J Neurotrauma 1995; 12:903-6.
28. Readnower R D, Chavko M, Adeeb S, et al. Increase in blood-brain barrier permeability, oxidative stress, and activated microglia in a rat model of blast-induced traumatic brain injury. J Neurosci Res. 2010; 88:3530-9
29. Garman R H, Jenkins L W, Switzer R C, et al: Blast exposure injury in rats with body protection is characterized primarily by diffuse axonal injury. J Neurotrauma 2011; 28:947-959
30. Shear D A, Lu X C, Pedersen R, Wei G, Chen Z, Davis A, Yao C, Dave J, Tortella F C. Severity profile of penetrating ballistic-like brain injury on neurofunctional outcome, blood-brain barrier permeability, and brain edema formation. J Neurotrauma. 2011; 28:2185-95.
31. Marion D W, Curley K C, Schwab K, Hicks R R. mTBI Diagnostics Workgroup. Proceedings of the military mTBI Diagnostics Workshop, St. Pete Beach, J Neurotrauma. 2011 April; 28(4):517-26
32. Management of Concussion/mTBI Working Group. VA/DoD Clinical Practice Guideline for Management of Concussion/Mild Traumatic Brain Injury. J Rehabil Res Dev 2009; 46(6):CP1-68
33. Finkelstein E, Corso P, Miller T, et al: The Incidence and Economic Burden of Injuries in the United States. New York (NY): Oxford University Press; 2006
34. Coronado, McGuire, Faul, Sugerman, Pearson. The Epidemiology and Prevention of TBI 2012

35. Taylor B C, Hagel E M, Carlson K F, Cifu D X, Cutting A, Bidelspach D E, Sayer N A. Prevalence and costs of co-occurring traumatic brain injury with and without psychiatric disturbance and pain among Afghanistan and Iraq War Veteran V.A. users. Med Care. 2012; 50(4):342-6.

36. National Institute of Neurological Disorders and Stroke (1989, February) Interagency Head Injury Task Force Report. Bethesda, Md.

37. Anslyn E V & Dougherty D A (2006) Modern physical organic chemistry (University Science, Sausalito, Calif.) pp xxviii, 1095 p 38. Turro N J, Ramamurthy V, & Scaiano J C (2010) Modern Molecular Photochemistry of Organic Molecules (University Science Books, Sausalito, Calif.) p 1084

39. The Molecular Probes® Handbook—A Guide to Fluorescent Probes and Labeling Technologies 40. Jöbsis, Frans F., Noninvasive, Infrared Monitoring of Cerebral and Myocardial Oxygen Sufficiency and Circulatory, Science, Vol. 198, No. 4323 (Dec. 23, 1977), pp. 1264-1267

41. IEC 60601-2-33 Requirements for the Safety of MR Equipment for Medical Diagnostics 42. Sinz E H, Kochanek P M, Dixon C E, et al: Inducible nitric oxide synthase is an endogenous neuroprotectant after traumatic brain injury in rats and mice. J Clin Invest 104:647-656, 1999

43. Tehranian R, Rose M E, Vagni V, et al: Transgenic mice that overexpress the anti-apoptotic Bcl-2 protein have improved histological outcome but unchanged behavioral outcome after traumatic brain injury. Brain Res 26:1101: 126-135, 2006

44. Shellington D K, Wu X, Exo J, et al: Acute volume-limited fluid resuscitation with polynitroxylated pegylated hemoglobin attenuates neuronal death after combined traumatic brain injury and hemorrhagic hypotension in mice. Crit Care Med 39:494-505, 2011

45. Williams C, Mehrian Shai R, Wu Y, Hsu Y H, Sitzer T, Spann B, McCleary C, Mo Y, Miller C A. Transcriptome analysis of synaptoneurosomes identifies neuroplasticity genes overexpressed in incipient Alzheimer's disease. PLoS One. 2009; 4(3):e4936

46. Pratap M, Olsen R W, Otis T S, Wallner M. 2009. Etomidate, propofol and the neurosteroid THDOC increase the GABA efficacy of recombinant $\alpha 4\beta 3\delta$ and $\alpha 4\beta 3$ GABAA receptors expressed in HEK cells. Neuropharmacology. 56:155-160

47. Meera P, Wallner M, Song M, Toro L. 1997. Large conductance voltage- and calcium-dependent K+ channel, a distinct member of voltage-dependent ion channels with seven N-terminal transmembrane segments (S0-S6), an extracellular N terminus, and an intracellular (S9-S10) C terminus. Proc Natl Acad Sci USA 94:14066-14071

48. Mordwinkin N M, Meeks C J, Jadhav S S, Espinoza T, Roda N, Dizerega G S, Louie S G, Rodgers K E. Angiotensin-(1-7) administration reduces oxidative stress in diabetic bone marrow. Endocrinology. 2012 May; 153(5): 2189-97.

49. Bayir H, Kagan V E, Borisenko G G, Tyurina Y Y, Janesko K L, Vagni V A, Billiar T R, Williams D L, Kochanek P M. Enhanced oxidative stress in iNOS-deficient mice after traumatic brain injury: support for a neuroprotective role of iNOS. J Cereb Blood Flow Metab 25:673-684, 2005

50. Whalen M J, Carlos T M, Dixon C E, Wisniewski S R, Schiding J K, Clark R S B, Baum E, Marion D W, Kochanek P M: Effect of Traumatic Brain Injury in Mice Deficient in Intercellular Adhesion Molecule-1: Assessment of Histopathologic and Functional Outcome. J Neurotrauma 16:299-309, 1999

51. Tehranian R, Rose M E, Vagni V, Pickrell A M, Griffith R P, Liu H, Clark R S B, Dixon C E, Kochanek P M, Graham S H. Disruption of bax protein prevents neuronal cell death but produces cognitive impairment in mice following traumatic brain injury. J Neurotrauma 25:755-767, 2008

52. Haselkorn M L, Shellington D, Jackson E K, Vagni V, Janesko-Feldman K, Dubey R K, Gillespie D G, Cheng D, Bell M J, Jenkins L W, Homanics G, Schnermann J, Kochanek P M: Adenosine A1 receptor activation as a brake on microglial proliferation after experimental traumatic brain injury in mice. J Neurotrauma 27:901-10, 2010. PMC2943944

53. Foley L M, Hitchens T K, Melick J, Bayir H, Ho C, Kochanek P M: Effect of inducible nitric oxide synthase on cerebral blood flow after experimental traumatic brain injury in mice. J Neurotrauma 25:299-310, 2008

54. Hendrich K S, Kochanek P M, Melick J A, Schiding J K, Statler K D, Williams D S, Marion D W, Ho C: Cerebral perfusion during anesthesia with fentanyl isoflurane or pentobarbital in normal rats studied by arterial spin-labeled MRI. Magn Reson Med 46:202-206, 2001

55. Kochanek P M, Hendrich K S, Dixon C E, Schiding J K, Williams D S, Ho C: Cerebral blood flow at one year after controlled cortical impact in rats: assessment by magnetic resonance imaging. J Neurotrauma. 2002 September; 19(9):1029-37

56. Blasiole B. Bayir H, Vagni V, Janesko-Feldman K, Wisniewski S R, Chiekhi A, Long J, Atkins J, Kochanek P M. 100% Oxygen is beneficial during resuscitation of experimental combined traumatic brain injury and hemorrhagic shock in mice. ATACCC Annual Meeting Aug. 15-19, 2011

57. Manole M, Kochanek P, Foley L, Hitchens T, Bayir H, Alexander H, Garman R, Ma L, Hsia C, Clark R: Polynitroxil albumin and albumin therapy after pediatric asphyxial cardiac arrest: Effects on cerebral blood flow and neurological outcome. J Cereb Blood Flow Metab 2011 Nov. 30. [Epub ahead of print]

58. Coronado V G, Thurman D J, Greenspan A I, Weissman B M. Epidemiology. In: Jallo J. Loftus C M, eds. Neurotrauma and critical care: brain. New York, N.Y.: Thieme; 2009:3-19.

59. Faul M, Xu L, Wald M M, Coronado V. Traumatic brain injury in the United States: emergency department visits, hospitalizations, and deaths, 2002-2006. Atlanta, Ga.: CDC, National Center for Injury Prevention and Control; 2010

60. Turro N J, Ramamurthy V and Scaino J C (2010) Modern Molecular Photochemistry of Organic Moleculse. University Science Books, Sausalito, Calif.

The invention claimed is:

1. A method comprising
administering a photoacid compound to a biological environment, wherein the photoacid compound comprises a caged compound and a light absorbing moiety, the caged compound being caged with the light absorbing moiety having an absorption wavelength greater than or equal to 750 nm; and
irradiating the biological environment to excite the light absorbing moiety with light at a wavelength in a range from 900-1100 nm, thus releasing the caged compound wherein the photoacid compound is represented according to formula (I):

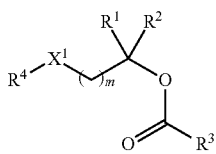

(I)

wherein: $R^4$ is the light-absorbing moiety presenting a hydroxyl group for interaction with the carbonyl oxygen of $R^3(CO)O$, wherein the light-absorbing moiety is a substituted or unsubstituted polycyclic aromatic hydrocarbon containing 2 to 7 aromatic rings, a substituted or unsubstituted closed chain cyanine, or a substituted or unsubstituted hemicyanine, and wherein the hydroxyl group is covalently bonded to the polycyclic aromatic hydrocarbon or closed chain cyanine or hemicyanine and is ortho to $X^1$; $R^3$ is the caged compound, wherein the caged compound is substituted or unsubstituted alkyl, aryl, heteroaryl, aminoalkyl, or oxyalkyl moiety; $X^1$ is independently selected from the group consisting of C and O; m is between 0 and 3; and $R^1$ and $R^2$ are independently $C_1$-$C_6$ alkyl groups, cycloalkyl, or substituted or unsubstituted hydrocarbylene groups wherein when $R^1$ and $R^2$ are substituted or unsubstituted hydrocarbyl groups they are linked together to form a cyclic moiety.

2. The method of claim 1, wherein the light absorbing moiety is able to absorb light at a wavelength of from about 900 nm to about 1100 nm.

3. The method of claim 1 wherein R1 and R2 are methyl groups.

4. The method of claim 1, wherein the biological environment is a body part of an individual and the administering is performed by systemic or topic administration of the photoacid compound.

5. The method of claim 4, wherein the biological environment exhibits inflammation or an inflammatory response.

6. The method of claim 1, wherein the caged compound is a drug or imaging agent.

7. The method of claim 1, wherein the irradiating is performed by a wearable infrared emitting device suitable to worn around a body part of an individual.

* * * * *